US005374237A

United States Patent [19]

McCarty, Jr.

[11] Patent Number: 5,374,237

[45] Date of Patent: Dec. 20, 1994

[54] THERAPEUTIC METHOD AND APPARATUS FOR EFFECTING TRANSLATORY CONTINUOUS PASSIVE MOTION OF THE TEMPOROMANDIBULAR JOINT

[76] Inventor: William L. McCarty, Jr., 2021 Normandie Dr., Montgomery, Ala. 36198

[21] Appl. No.: 919,961

[22] Filed: Jul. 27, 1992

Related U.S. Application Data

[63] Continuation-in-part of Ser. No. 628,177, Dec. 17, 1990, abandoned.

[51] Int. Cl.[5] .................. A61F 5/00

[52] U.S. Cl. .................. 601/38; 601/23

[58] Field of Search .................. 128/24 R, 24.1, 24.2, 128/24.5, 25 R, 44–46, 48, 49, 51, 52, 56, 62 A; 433/69, 73, 229, 19, 69; 602/17; 601/1, 15, 18, 23, 38

[56] References Cited

U.S. PATENT DOCUMENTS

| | | | |
|---|---|---|---|
| 1,466,559 | 8/1923 | Purdy . | |
| 1,709,122 | 4/1929 | Fouts | 128/52 |
| 1,953,088 | 4/1934 | Purdy . | |
| 2,095,956 | 10/1937 | Bess | 128/52 |
| 4,134,169 | 1/1979 | Sinclair | 128/62 A |
| 4,457,708 | 7/1984 | Dufour . | |
| 4,568,280 | 2/1986 | Ahlin . | |
| 4,577,627 | 3/1986 | Garcia . | |
| 4,639,220 | 1/1987 | Nara et al. | 433/69 |
| 4,671,766 | 6/1987 | Norton . | |
| 4,700,695 | 10/1987 | Davis et al. . | |
| 4,723,854 | 9/1988 | Weber | 433/69 |
| 4,744,556 | 5/1988 | Shaffer . | |
| 4,810,192 | 3/1989 | Williams | 433/6 |
| 4,883,046 | 11/1989 | Fontenot . | |
| 4,909,502 | 3/1990 | Beeuwkes, III et al. . | |
| 4,955,367 | 9/1990 | Homsy . | |

FOREIGN PATENT DOCUMENTS

| | | | |
|---|---|---|---|
| 384686 | 1/1921 | Germany | 128/51 |
| 151137 | 9/1920 | United Kingdom . | |

*Primary Examiner*—Richard J. Apley
*Assistant Examiner*—Linda C. Dvorak
*Attorney, Agent, or Firm*—Kenneth E. Darnell

[57] ABSTRACT

A therapeutic method for rehabilitating the temporomandibular joint by induction of translatory motion of the joint either post-operatively or as therapy for a variety of conditions, the invention also contemplates apparatus capable of practicing the present method by continuously and passively moving the joint in a translatory sense.

43 Claims, 16 Drawing Sheets

THERAPEUTIC METHOD AND APPARATUS FOR EFFECTING TRANSLATORY CONTINUOUS PASSIVE MOTION OF THE TEMPOROMANDIBULAR JOINT

CROSS-REFERENCE TO RELATED APPLICATION

This application is a continuation-in-part of U.S. patent application Ser. No. 07/628,177, filed Dec. 17, 1990, by William L. McCarty, Jr., the parent application being abandoned as of the filing date of this application.

BACKGROUND OF THE INVENTION

1. Field of the Invention

The invention relates generally to therapy of the temporomandibular joint and particularly to a method and apparatus for providing therapeutic treatment of the joint.

2. Description of the Prior Art

Surgery is often required to correct internal derangements of the temporomandibular joint. Post-operative care has varied widely with little agreement among clinicians as to the most effective manner of managing such care. A common practice involves loose intermaxillary fixation for the first one or two days following surgery. However, this practice does little more than prevent damage to the joint especially if the patient becomes nauseated after surgery. After removal of fixation it has been fairly common practice to initiate limited motion typically in rotation. Such procedures have ranged from having the patient put his thumb between the upper and lower incisors to guide him in measuring jaw opening and also to allow him to judge the desired degree of limitation. Recently, an apparatus capable of providing continuous passive motion in rotation, that is, the opening and closing of the mouth, has been available from Vitech, Inc. of Houston, Tex. and has been marketed under the trademark "Trans-Jaw". A product similar to the "Trans-Jaw" has been distributed by the Therabite Corporation of Bryn Mawr, Pa. and is referred to by the trademark "Therabite". The "Therabite" product is intended to provide rotational motion for the purpose of improving mandibular range of motion. These and other therapeutic methods and apparatus have been employed but with limited success. Many other conditions involving disorders of the temporomandibular joint have also been treated to less than satisfactory conclusions due to deficiencies in state of the art treatment methodology. Such conditions include both rehabilitation situations following arthroscopy, fractures and/or trauma, osteoarthritis and even relatively routine rehabilitation of stiff, painful jaw joints. In these conditions and in other conditions including open joint surgery such as arthroplasty, meniscectomy and total joint replacement, as examples, methodology relating to rehabilitation has been limited in part by a lack of understanding of the complexity of the general subject of temporomandibular joint disorders as well as a lack of progress in this area directed to truly effective rehabilitative procedures and apparatus capable of assisting in time practice of such procedures.

The present invention provides an effective therapeutic method and an apparatus capable of practice of the method, the invention providing a substantial advance in the art of rehabilitative care post-operatively, post-trauma and also in rehabilitative treatment of chronic and acute disorders involving the temporomandibular joint.

SUMMARY OF THE INVENTION

The invention provides a novel therapeutic method for rehabilitation of the temporomandibular joint, hereinafter often referred to as TMJ, by the induction of translatory notion of the joint. The therapeutic methodology of the invention can be applied post-operatively in open joint surgery situations including arthroplasty, meniscectomy, total joint replacement, ankylosis, etc. Further, the rehabilitative methodology of the invention can also be applied after arthroscopy, after fractures and/or trauma and as treatment for various diseases affecting the TMJ such as osteoarthritis, etc. and for routine rehabilitation of stiff, painful jaw joints and the like. The present therapeutic methodology preferably involves continuous passive motion of the mandible in a translatory sense. This translatory movement of the mandible with the resulting translation of the TMJ biaxially significantly improves upon prior treatment modalities involving only rotation of the joint. Treatment according to the present method results in more rapid rehabilitation of the TMJ with a patient regaining maximum potential use of the joint more rapidly and with greater facility than with prior rehabilitative techniques.

The invention further provides various embodiments of apparatus for effecting translatory motion of the temporomandibular joint in a continuous and passive manner. The apparatus of the invention effectively comprises continuous passive motion devices which move the mandible without the requirement for exertion on the part of the patient other than to close in order to engage those portions of the apparatus held within the mouth of the patient. Motion of the TMJ is thus effected in rehabilitative therapy even prior to the time within which the patient could move the mandible voluntarily. Preferred embodiments of the apparatus take the form of hand-held devices which drive a plate element in a translatory motion through use of various forms of cam-like eccentric arrangements. In one embodiment, the "throw" or degree of motion afforded the plate element is infinitely adjustable within a predetermined range of motion. In the several embodiments, the plate element receives a registration on a distal end thereof formed as an impression in an acrylic material mounted distally of the plate element and configured to be received within the mouth of a user with the registration receiving the teeth of the lower jaw. A second plate element opposing the first-mentioned plate element is provided with a registration of the teeth of the upper jaw and effectively acts to hold the apparatus within a frame of reference with only the mandible being moved to effect the therapeutic method of the invention.

As is defined herein and as is apparent from the description of the invention, translatory motion has components of motion in both side-to-side and front-to-back senses and encompasses such motions. The use of translatory motion therapeutically is herein described in detail and forms the basis for the methods and apparatus herein disclosed.

Accordingly, it is an object of the invention to provide a therapeutic method and apparatus for rehabilitation of the temporomandibular joint through induction of translatory motion of the joint, the methodology and apparatus of the invention being useful post-operatively or pre-operatively in rehabilitative therapy involving a variety of conditions, diseases and disorders affecting the temporomandibular joint.

It is another object of the invention to provide methodology and apparatus capable of treatment of the temporomandibular joint through continuous passive motion of the joint in a translatory sense.

It is a further object of the invention to provide therapeutic methodology and apparatus capable of effecting rehabilitative treatment of surgery of the temporomandibular joint including arthroplasty, meniscectomy, total joint replacement and the like and including rehabilitation of disease conditions including osteoarthritis and the like as well as post-arthroscopic conditions and conditions including fractures and/or trauma with resultant adhesions as well as routine rehabilitation of stiff, painful jaw joints.

Other objects and advantages of the invention will become more readily apparent in light of the following detailed description of the preferred embodiments.

DESCRIPTION OF THE PREFERRED EMBODIMENTS

Figure 1:
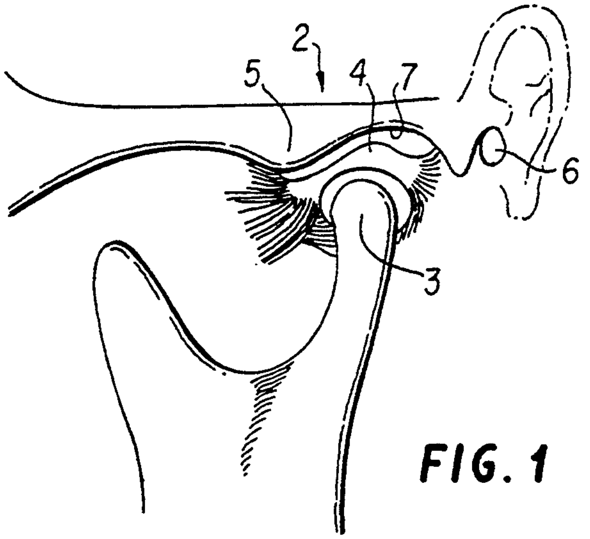
FIG. 1 is a schematic illustrating a sagittal section of a healthy temporomandibular joint.
Figure 2:
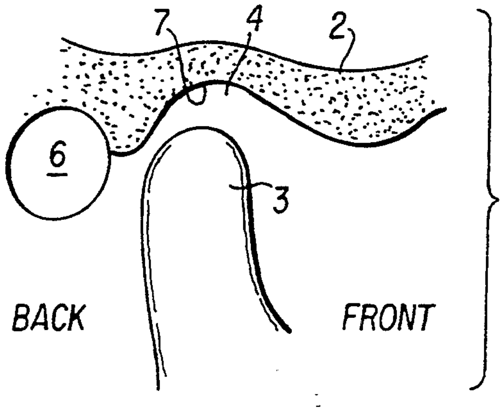
FIG. 2 is a schematic illustrating a lateral view of a temporomandibular joint prior to forward translation.
Figure 3:
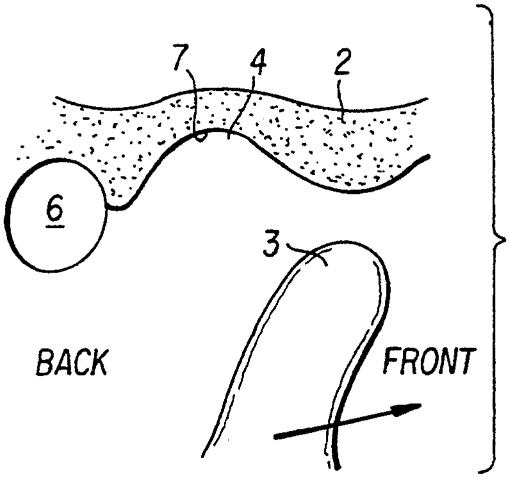
FIG. 3 is a schematic illustrating a lateral view of translation in a forward direction of a temporomandibular joint.
Figure 4:
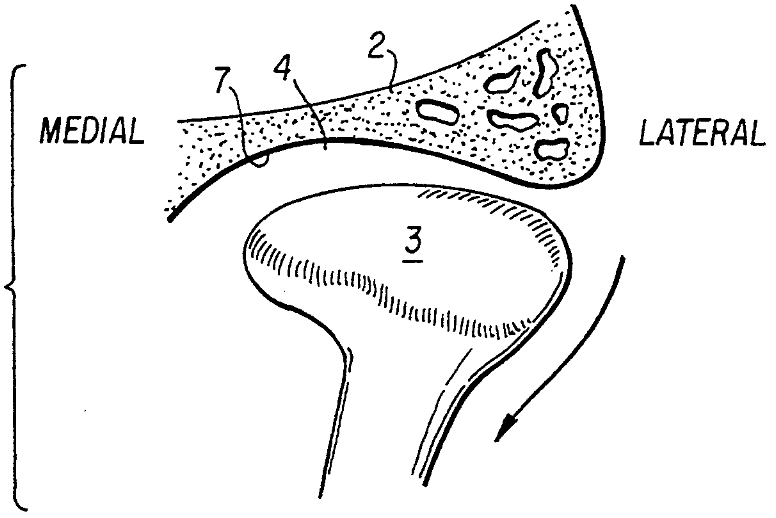
FIG. 4 is a schematic illustrating a frontal view of the condyle translating forwardly in the fossa.
Figure 5A:
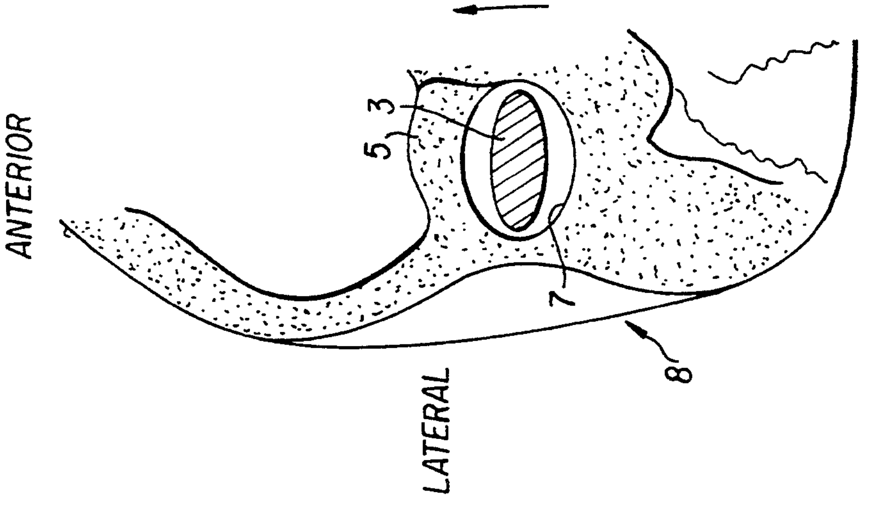
FIG. 5A, 5B and 5C are schematics illustrating translation of the temporomandibular joint as seen from the base of the skull.
Figure 5B:
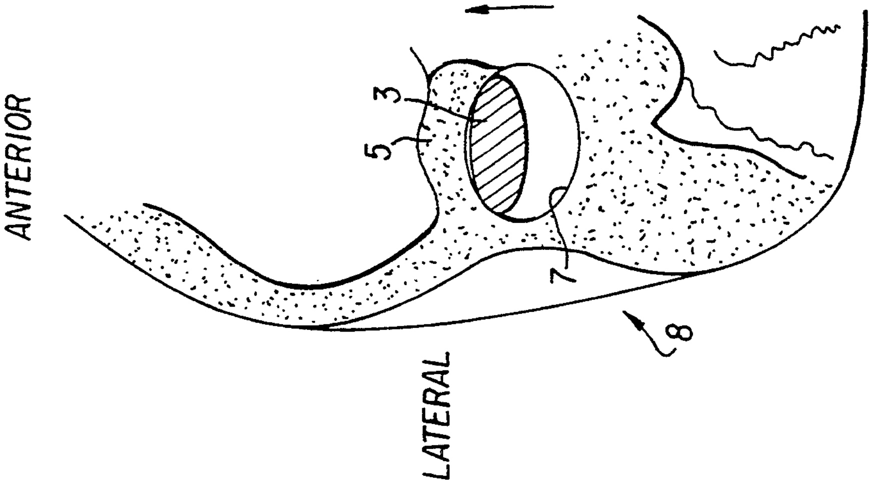
Figure 5C:
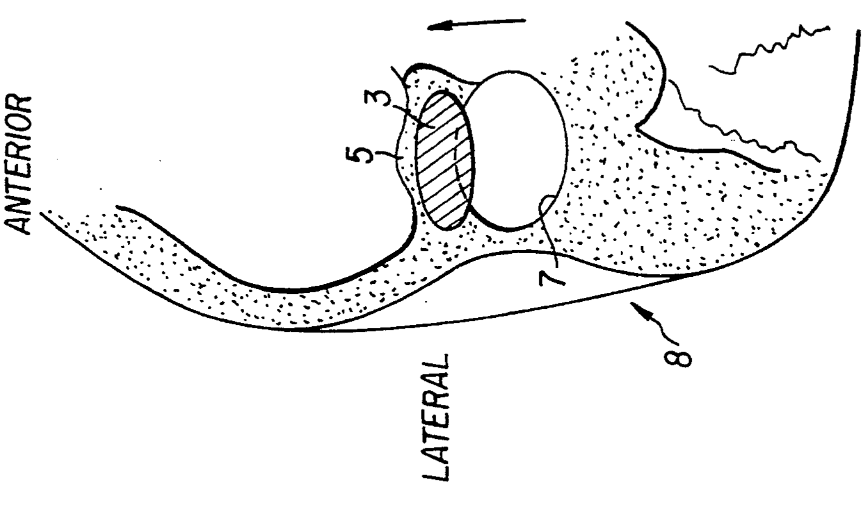

Referring now to the drawings and particularly to FIG. 1, the temporomandibular joint is illustrated in sagittal section so that further reference herein to the temporomandibular joint can be better appreciated. The joint as seen in FIG. 1 is a healthy joint and is shown in order to relate the various portions of the joint and surrounding structures to the following discussion of translatory motion of the joint. The mandible is seen at 1 to include the condyle 3 which opposes the disc 4 in the temporal portion of zygomatic arch 2. The articular eminence is shown at 5. The glenoid fossa 7 is seen to lie between the articular eminence 5 and the ear canal 6. FIGS. 2, 3 and 4 illustrate translation of the condyle 3 from a back position as seen in FIG. 2 to a forward translatory position as seen in FIG. 3. FIGS. 2 and 3 illustrate translatory motion from a lateral view. FIG. 2 represents the "back" position and FIG. 3 represents the "front" position with the condyle 3 translating forwardly. FIG. 4 provides a frontal view of the condyle 3 translating forwardly Within the fossa 7. As can further be appreciated by reference to FIGS. 5A, 5B and 5C wherein translation of the TMJ is seen from the base of the skull, the first motion of the temporomandibular joint from the closed position of FIG. 5A is, on opening of the mouth, a rotation up to approximately 25 mm of interincisal opening as seen in FIG. 5B. In order for the jaw to open any further after a rotation of approximately 25 mm, the jaw must translate forwardly and downwardly such as to the position of FIG. 5C which corresponds to the opening illustrated in FIG. 3. Again referring to FIGS. 2 and 3, the condyle 3 translates down the slope of the articular eminence 5, over the midslope and into the anterior recess forward of the articular eminence 5. The motion thus described is normal motion. However, following surgery, arthroscopy and/or other traumatic events, translation does not tend to occur readily especially when opening is emphasized as therapy. In such conventional situations, either decreased or no translation occurs and a patient soon loses the ability to translate the joint. The loss of ability to translate occurs due to adhesion formation, primarily in the anterior recesses and also due to the formation of tough, fibrous adhesions between the tympanic plate (not shown) and redundant soft tissue in the posterior of the condyle. As these fibrous tissues bind down to the pitted bearing surfaces of the condyle 3 and fossa 7, degenerative changes occur with resultant fibrous ankylosis, degenerative joint disease and the further opportunity for formation of a bony ankylosis.

The present methodology thus teaches rehabilitation of the temporomandibular joint by effecting translatory motion of the joint and particularly by effecting such translatory motion continuously and passively. By effecting translatory motion, the joint is less likely to form adhesions and is further less likely to degenerate with resultant fibrous ankylosis, etc. Further, translation of the temporomandibular joint does not cause the degree of muscle spasm which occurs through the use of therapy which emphasizes opening or rotation. Translation can also be achieved in a gentle manner which does not overload the masticatory muscles. While rotation or opening can be employed in the rehabilitation of the joint, emphasis on translation according to the invention results in at least some opening of the mouth, such opening occurring naturally either during effectation of translation or otherwise. Opening is usually enhanced by virtue of translation.

In motion provided continuously and passively through use of the apparatus of the invention, the motion imparted to the mandible invariably has both a component of motion in a side-to-side sense and a component of motion in a front-to-back sense. The method of the invention thus provides for translatory motion of the temporomandibular joint as described herein. The invention further provides for translatory motion both continuously and passively through use of the apparatus of the invention. The several embodiments of the apparatus of the present invention are capable of effecting translatory motion necessary for rehabilitation of the temporomandibular joint, the apparatus essentially comprising devices which will generally be referred to as CPM devices and which function to effect movement of the temporomandibular joint both continuously and passively. The passive motion effected by the apparatus of the invention is, of course, of paramount importance.

Referring now to FIGS. 6 through 14, a first embodiment of the present apparatus is seen generally at 10 to include a power source/motor unit 12 which can conveniently be grasped by a user. The unit 12 can take the form of any of a number of rechargeable, hand-held, typically battery-powered devices such as are commercially available. The unit 12 can simply comprise a motor unit with the power source being connected to the motor unit but provided at a remote location. While not shown in the drawings, the unit 12 includes a replaceable and/or rechargeable battery which powers an electric motor (not shown) disposed internally of the unit 12. The electric motor directly drives female coupling 14 which Call take the form of an adjustable chuck or similar connector which receives a shaft as will be described hereinafter. The unit 12 is preferably reversible in order that the coupling 14 call be driven in both clockwise and counter-clockwise rotation. The unit 12 typically rotates the coupling 14 at a rate of approximately 120 to 150 rpm, a rotational rate of approximately 130 rpm being commonly employed. It should be understood that the initial rotational rate provided by the unit 12 can be geared down in a conventional manner such that the "speed" of the apparatus can be chosen as desired. The unit 12 could be configured to provide a rotational rate of less than 30 rpms, for example, which could be converted to translatory motion within the apparatus 10 without a gearing down from a higher rotational speed. However, motor units 12 are readily available as rechargeable, battery-powered devices having rotational speeds of approximately 150 rpm. Accordingly, it becomes convenient to select such a unit 12 for convenience and economy. In a preferred practice of the present method, the rotational speed which will be converted to translatory motion within the apparatus 10 is preferably on the order of 25 to 30 revolutions per minute and can vary within a range of revolutions per minute with determining factors being the physical and emotional comfort of the patient when using the apparatus 10. While the apparatus 10 can be driven at speeds at only a few revolutions per minute on the low side, and over 35 revolutions per minute, for example, on the high side, a general range of about 8 to 35 revolutions per minute is preferred in practice since a patient is not intimidated by such a speed and the therapy progresses at a satisfactory rate at such angular speeds.

In order to reduce the rotational rate typically provided by commercially available battery/motor units, a gear reduction box is provided as will be described hereinafter. As noted above, the power source/motor unit 12 can be configured to provide a rotational output which is directly used in the apparatus 10 without the necessity for the reduction gearbox. For purposes of economy and convenience, however, the relatively inexpensive battery/motor combinations used for powering electric screwdrivers and the like can be used, devices of this nature usually requiring a reduction of rotational rate for use within the present environment.

Figure 6:
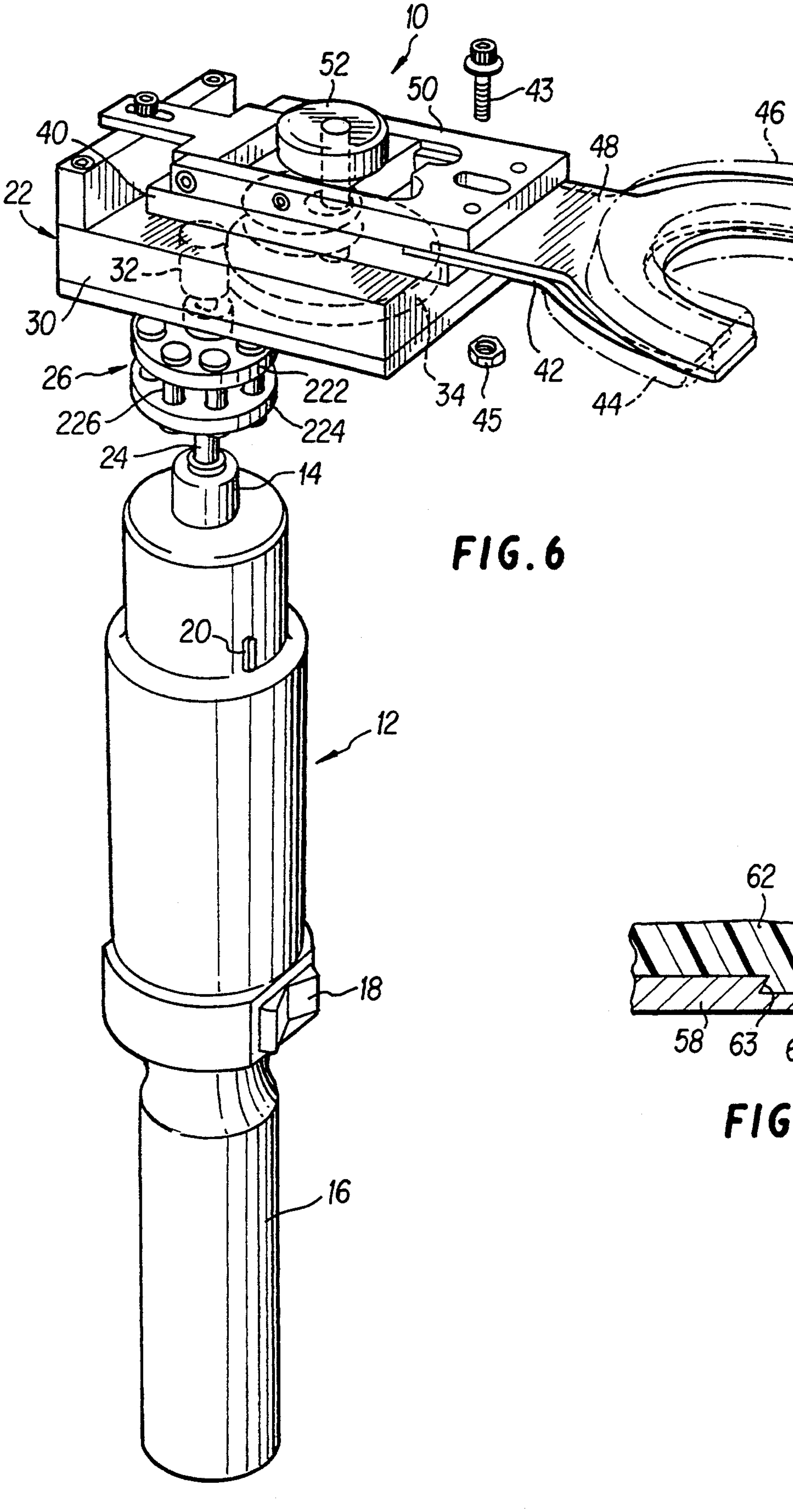
FIG. 6 is a perspective view of a first embodiment of the apparatus of the invention.

With continuing reference to FIG. 6, the power source/motor unit 12 is further seen to include a handle 16. A switch 18 mounted on the unit 12 is used to select either clockwise or counter-clockwise operation of the unit 12. A safety stop element 20 mounted on the unit 12 can be depressed to inhibit rotation of the coupling 14, the stop element 20 being one safety feature of the apparatus. A further safety feature is provided by the switch 18 which only causes actuation of the unit 12 and thus rotation of the coupling 14 when actually depressed by a user. In other words, release of finger pressure from the switch 18, regardless of rotational direction, discontinues rotation of the coupling 14 and thus operation of the apparatus 10. It is to be understood that the structure thus noted as comprising the power source/motor unit 12 is conventional.

The apparatus 10 is now seen to comprise a translatory drive unit 22 which is driven by the power source/motor unit 12. Although not shown in the drawings, a cover can be formed over the unit 22 for the sake of convenience and appearance. The unit 22 can be readily mounted to and demounted from the unit 12 as will be described in greater detail hereinafter. The translatory drive unit 22 receives rotary motion from the unit 12 at a rate such as that referred to above and converts this rotary motion first to a reduced rotary motion and then to a translatory motion which is directly imparted to the mandible of a user in order to move the temporomandibular joint of the user in a translatory fashion.

The translatory drive unit 22 connects to the unit 12 by means of shaft 24 which is received within the coupling 14. As is conventional in that art relating to portable, battery-powered motor drive units as referred to above, the shaft 24 is of a size which fits flushly and snugly into the coupling 14 without the requirement for providing an adjustable chuck although such an adjustable coupling could be employed if desired. The shaft 24 connects to and transmits motion through a joint 26 which can conveniently take the form of any suitably sized universal joint which will allow some degree of "play" between the translatory drive unit 22 and the unit 12 so as to render the apparatus 10 more comfortable and convenient for use by a patient. The joint 26 connects at its other end with a shaft 28 which is not readily seen in FIG. 6 but which can be seen in FIG. 7 inter alia. The shaft 28 extends into reduction gearbox 30 and is coupled to a 25-tooth gear 32 which drives 100-tooth gear 34, the gears 32 and 34 being shown in other figures including FIGS. 7 and 8. The reduction gearbox 30 reduces the rotational speed of the shaft 28 in a 4:1 ratio, shaft 36 exiting the reduction gearbox 30 rotating at a speed of one revolution per minute for each four revolutions per minute of the shaft 28 which entered the gearbox 30. As with much of the structure referred to in this general discussion of FIG. 6, the shaft 36 is not easily seen in FIG. 6 but can be seen in FIG. 7 inter alia.

Rotation of the shaft 36 drives a double eccentric arrangement 38 best seen in FIGS. 7, 12 and 13 inter alia and which will be described in detail hereinafter. The double eccentric arrangement 38 couples to drive bar 40 which mounts a yoke-shaped plate 42 for movement in an eliptical fashion. The yoke-shaped plate 42 has a registration 44 formed of an acrylic material cured by ultraviolet radiation to yield an impression of the teeth or other structure associated with the mandible of a user. The teeth of the mandible or lower jaw are thus received into the registration 44 mounted to the plate 42. Similarly, the teeth of the upper jaw are received within registration 46 formed of an acrylic material cured by ultraviolet radiation from a direct impression of the teeth or other structure of the upper jaw, this registration 46 being carried by yoke-shaped plate 48. The plate 48 is fixed to a stationary bar 50, the bar 50 being adjustable relative to the drive bar 40. The drive bar 40 and stationary bar 50 are effectively received on the shaft 36, the shaft 36 extending above the stationary bar 50 and having mounting cap 52 received thereon to hold the assembly of the drive bar 40 and stationary bar 50 together. The mounting cap 52 connects fixedly to the shaft 36 by means of a set screw 54 as best seen in consideration of both FIGS. 7 and 11.

Figure 7:
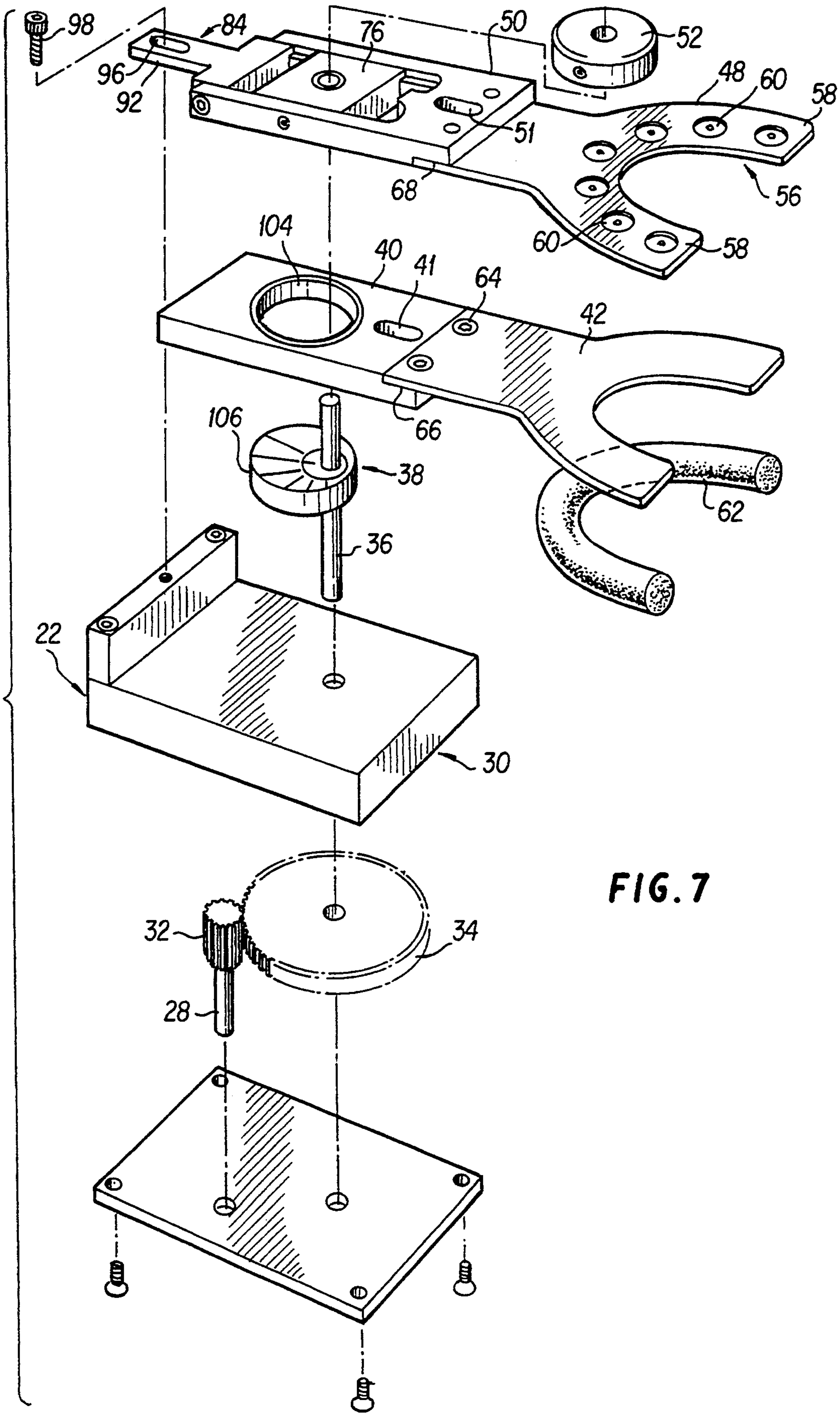
FIG. 7 is an exploded view in perspective of the apparatus of FIG. 6 less the power source and motor.
Figure 8:
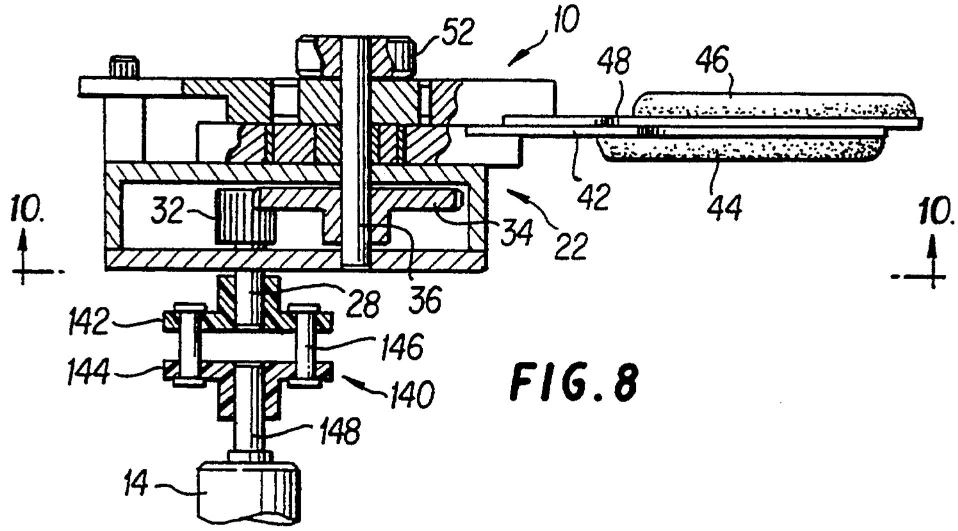
FIG. 8 is an elevational view in partial section of the apparatus of FIG. 6 less the power source and motor.
Figure 9:
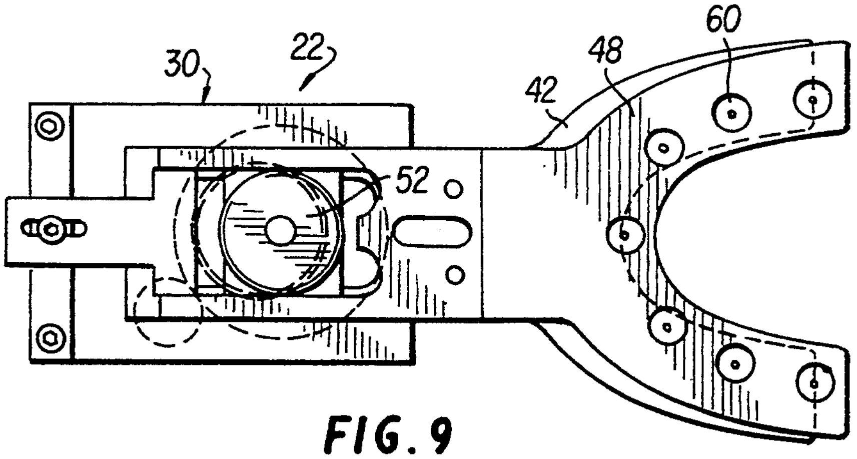
FIG. 9 is a plan view of the apparatus of FIG. 8.
Figure 10:
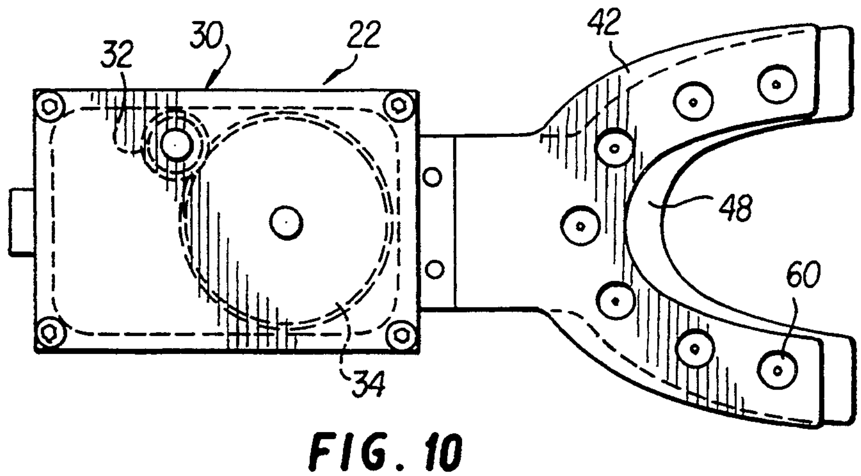
FIG. 10 is a sectional view of the apparatus of FIG. 8 taken along lines 10—10 of FIG. 8.
Figure 11:
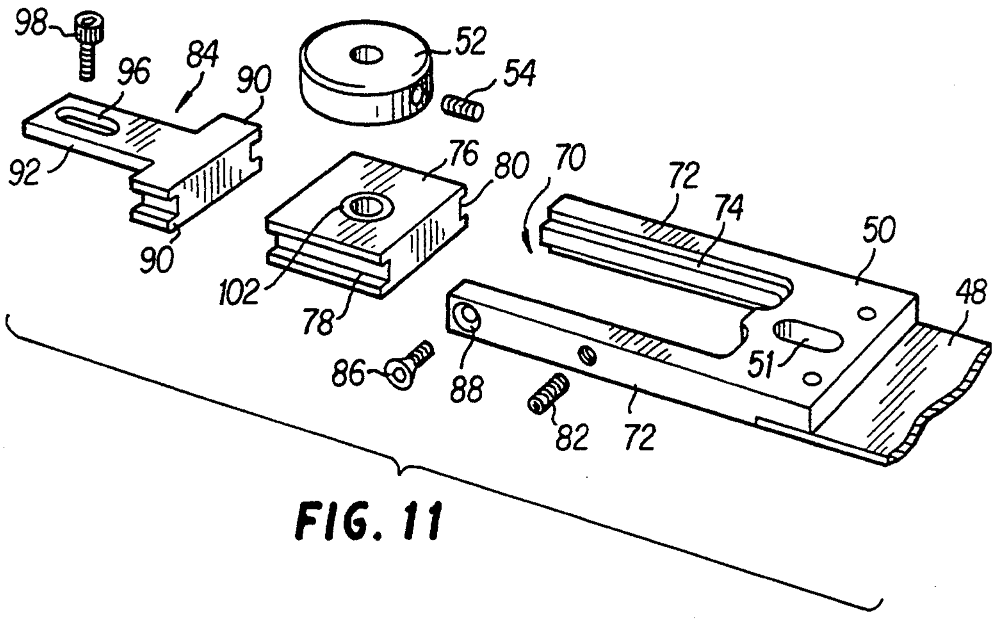
FIG. 11 is an exploded view of a detailed perspective of upper portions of the apparatus of FIG. 8.
Figure 12:
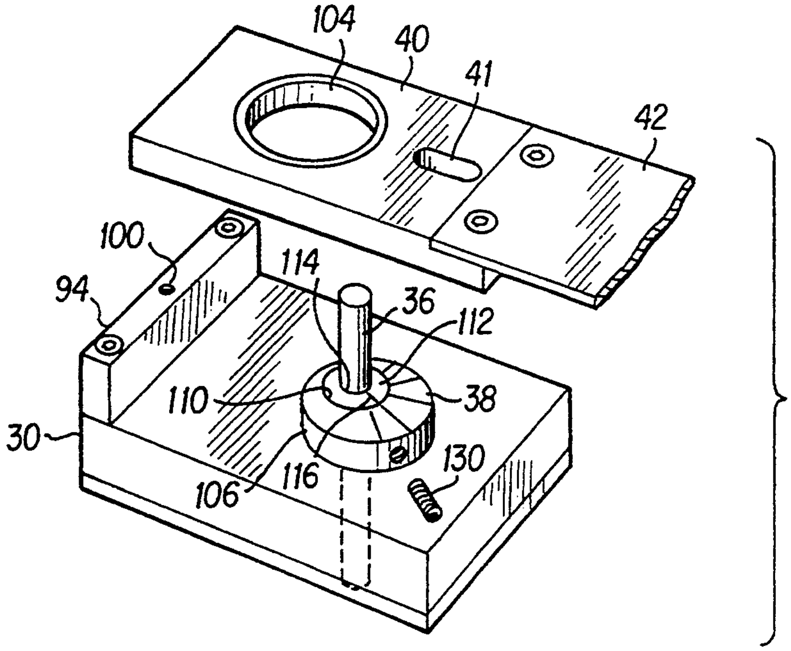
FIG. 12 is an exploded view of a detailed perspective of lower portions of the apparatus of FIG. 8.
Figure 13:
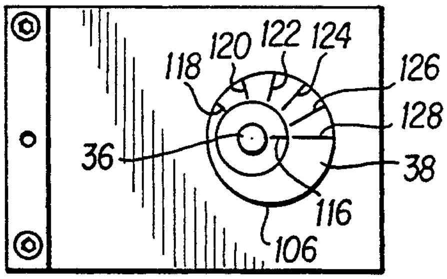
FIG. 13 is a plan view of a double eccentric arrangement seen also in FIG. 12.

Referring now to FIGS. 7, 11 and 12, the bars 40 and 50 are seen to be respectively formed with slots 41 and 51, said slots being alignable on removal from the unit 22 to facilitate formation of the registration 44 and 46. Screw 43 and nut 45, seen in FIG. 6, hold the bars 40 and 50 together so that impressions can be taken to form the registration 44 and 46. The screw 43 is inserted through the slots 41 and 51 and the nut 45 is used to hold the bars 40, 50 relative to each other while impressions are formed. The bars 40, 50 can be moved relative to each other with the screw 43 and nut 45 loosely attached until the bars 40, 50 are suitably positioned. The nut 45 is then tightened on the screw 43 to hold the bars 40, 50 together.

With this structural description of the apparatus 10 having now been provided, it can be seen in FIG. 6 that the registrations 44 and 46, and those portions of the plates 42 and 48 mounting said registrations, are received within the mouth of a user, the registration 44 receiving the teeth of the mandible while the registration 46 receives the teeth of the upper jaw. It is not necessary for all of the teeth to fit within the registrations 44 and 46, it only being necessary that the registrations 44 and 46 adequately "grip" or hold to the mandible and upper jaw respectively so that the apparatus 10 can function as required. The registrations 44 and 46 are not shown elsewhere in all of the drawings, not only for ease of illustration but also due to the necessity to show certain structure of the plates 42 and 48 as will be discussed hereinafter.

In operation, the registration 46 mounted on plate 48 stays in a fixed position along with the upper jaw of the user. The registration 44 connected through the plate 42 to the drive bar 40 and thus the double eccentric arrangement 38 is caused to move the mandible of a user in a manner such that any point of the plate 42 and thus of the registration 44 moves to define a substantially eliptical geometrical figure. This eliptical motion of the registration 44 causes translatory motion in the temporomandibular joint bilaterally. This translatory motion of the joints can be caused to occur over a range of motion varying from only slightly more than "no motion" to approximately 7 mm and even more depending upon the "throw" built into the double eccentric arrangement 38. Within the range of the double eccentric arrangement 38, the "throw" of the apparatus 10 can be infinitely varied in this embodiment of the invention. As a practical matter, the practitioner initiates treatment with a "throw" which results in approximately 1 to 2 mm of translatory motion of the temporomandibular joints with the degree of motion increasing with selection of different settings . At the termination of therapy, the throw of the apparatus 10 will typically be set in the range of 7 mm but can be more or less depending upon particular treatment situations. In a usual practice of the present methodology, the apparatus 10 is used for a period of approximately five to ten minutes for each treatment session with a total of approximately four treatment sessions each day. Accoding to desired treatment modalities, the period of each treatment session and the number of sessions can vary.

In a usual treatment situation, the apparatus 10 can be caused to operate more rapidly when the "throw", that is, the degree of motion imparted to the mandible, is low. As a practical matter, however, it is more convenient to adjust only the "throw" of the apparatus 10 and allow said apparatus 10 to operate at a constant "speed" regardless of the degree of the "throw".

The motion of the registration 44 must be forward of centric occlusion, that is, the motion imparted through the registration 44 to the mandible must be forward of the "bite" of the patient. In other words, this motion must be forward of the normal way in which the upper and lower teeth fit together. If motion is created behind centric occlusion, then the condyle 3 (shown in FIGS. 1–5) of the temporomandibular joint can be jammed into the tympanic plate (not shown) of the joint. The apparatus 10 is thus configured to prevent motion behind centric occlusion.

Figure 14:
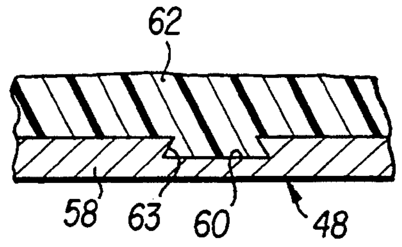
FIG. 14 is a side elevational view in section of a detailed portion of a registration mounted to a plate according to the invention.

Referring now to FIGS. 7 and 14, formation of the registration 46 on the yoke-shaped plate 48 can be appreciated. The plate 48 has a yoke portion 56 comprised of two arms 58, the arms 58 essentially forming a U-shaped structure which is sized to be received within the mouth and to accommodate the bite of a patient. Suitably shaped depressions 60 are seen to be formed in the upper surface of the arms 58. These depressions 60 receive portions of a rope 62 as can best be seen in FIG. 14, the rope 62 forming the registration 46 as will shortly be described. Once formed from the rope 62, the registration 46 connects to the plate 48 through flow of the acrylic material forming the rope 62/registration 46 into the depressions 60. The acrylic material used to form the registration 46, as well as the registration 44 which is formed in a substantially identical fashion, is an acrylic material marketed under the trademark "Triad" by Dentsply International, Inc. The acrylic material comes in the form of a "rope" as noted above by the reference to the rope 62. The rope 62 is formed to the shape of the arms 58 and then pressed onto the arm 58 with portions of the rope 62 flowing into the depressions 60. An impression is then taken in the rope 62 of the teeth of the upper jaw of the patient. This impression is then cured by means of ultraviolet radiation to form the registration 46. The registration 44 is formed in an essentially identical manner except that the impression is of the teeth of the lower jaw or mandible.

While it is not necessary to impress in the rope 62 all of the teeth of the patient, it is preferred to impress as many teeth as possible so that the registrations 44 and 46 will have maximum retentive capability to the mandible and upper jaw respectively. It is necessary to provide custom shaped indentations in the registrations 44 and 46 so that said registrations can be retained in the mouth during operation of the apparatus 10. It is also possible to form the depressions 60 with undercut areas 63 to facilitate attachment of the registrations 44 and 46 to the plates 42 and 48. However, attachment is satisfactory using substantially cylindrical depressions. The registrations 44 and 46 can be easily removed from the plates 42 and 48 by means of a wedging tool such as a screwdriver so that new registrations can be formed on said plates. Alternatively, the plates 42 and 48 can be formed of a "plastic" material and can be disposable items which are not reused.

The plates 42 and 48 are connected respectively to the drive bar 40 and the stationary bar 50 by means of set screws 64. It is desired to removably connect the plates 42, 48 to the bars 40, 50 so that the plates 42, 48 can be discarded if desired. Insets 66, 68 are respectively formed in upper and lower portions of the bars 40, 50 to receive anterior ends of said plates 42, 48.

Removal of the mounting cap 52 by loosening of the set screw 54 allows removal of the stationary bar 50 from the shaft 36. As best seen in FIG. 11, the stationary bar 50 is seen to be configured in a substantially rectangular solid shape having a cutout 70 located anteriorly of the bar 50, the cutout 70 being substantially rectangular in shape and being defined laterally by parallel opposed arms 72 which are portions of the bar 50. On interior surfaces of the arms 72 are located rails 74, one each of the rails 74 being disposed on one each of the arms 72. An adjustment plate 76 has U-shaped channels 78 and 80 formed on oppositely disposed sides of said plate 76, the channels 78 and 80 receiving the rails 74 therewithin for sliding movement of the adjustment plate 76 within the cutout 70. A set screw 82 extends through one of the arms 72 and its associated rail 74 to engage the adjustment plate 76 on a facing surface of the plate 76 defining the "floor" of the U-shaped channel 80. The set-screw 82 thus mounts the adjustment plate 76 in any desired position within the cutout 70. The location of the adjustment plate 76 within the cutout 70 is thus set by the practitioner according to the oral dimensions of the potential user.

A T-shaped mounting element 84 is received at the opening of the cutout 70 in the bar 50 and removably held therein by means of set screws 86 which extend through the sides of the arms 72 at distal ends thereof to be received into threaded apertures 88 formed one each at distal ends of arms 90 of the element 84. For ease of illustration, only one of the screws 86 is shown, the other screw 86 not being visible in FIG. 11. Leg 92 of the mounting element 84 extends to the surmounting position relative to vertical extension bar 94 which is mounted to the reduction gearbox 30 at the anterior end thereof. The height of the vertical extension bar 94 is dimensioned to accommodate the thickness of both the drive bar 40 and the stationary bar 50. Distally of the leg 92 a slot 96 is formed in said leg 92 so that machine screw 98 can be received within threaded aperture 100 formed at an upper face of the vertical exension bar 94 and medially of its length. Further adjustment of the location of the stationary bar 50 along its longitudinal axis is thus possible through use of the slot 96, the machine screw 98 mounting the assembly thus formed in association with the stationary bar 50 to the vertical extension bar 94 and thus to the reduction gearbox 30 which essentially forms a base structure for the translatory drive unit 22.

A brass bushing 102 is fitted centrally within the adjustment plate 76 and receives the shaft 36 therethrough. The stationary bar 50 and those structural elements associated therewith do not move during operation of the apparatus 10 but are maintained stationary relative to the upper jaw, the teeth of the upper jaw fitting into the registration 46 as aforesaid. The stationary bar 50 and that structure associated therewith also remains stationary relative to the movement of the drive bar 40 as will further be described hereinafter.

Referring again to FIG. 7 inter alia, the drive bar 40 is seen to be removably connected to the plate 42 in a manner substantially identical to the arrangement described relative to the stationary bar 50 and the plate 48. The anterior end of the plate 42 is received within the inset 66 and mounted to the drive bar 40 by means of set screws 64. It should be understood that the plate 42 and drive bar 40 (as well as the plate 48 and bar 50) can be formed unitarily. The drive bar 40 assumes the general conformation of a rectangular solid having a circular cutout 104 which receives circular major eccentric 106 therewithin. As is best seen in FIGS. 12 and 13, the major eccentric 106 is formed with an offset circular cutout 110 within which minor eccentric 112 is disposed. The minor eccentric 112 is provided with a circular aperture 114 offset from the center of the minor eccentric 112 for receiving the shaft 36 therethrough. The minor eccentric 112 is rigidly fixed to the shaft 36 by a press fit of said shaft 36 into the circular aperture 114. This fitting is such that the minor eccentric 112 does not turn on the shaft 36 but is fixed thereto. The double eccentric arrangement 38 is employed to set the "throw" of the translatory drive unit 22. A mark 116 is formed on the minor eccentric 112 essentially at the periphery of the eccentric 112 and on that diameter of the eccentric 112 which extends through the center of the circular cross-section of the shaft 36. Marks 118, 120, 122, 124, 126, and 128 are positioned about the periphery of the major eccentric 106 over a semicircular portion thereof as shown best in FIG. 13. Alignment of the mark 116 on the minor eccentric 112 with the mark 118 on the major eccentric 106 would essentially result in no motion of the drive bar 40. At the opposite extreme, alignment of the mark 116 on the minor eccentric 112 with the mark 128 on the major eccentric 106 will result in the greatest possible motion. While the mark 118 would not be directly utilized in a setting of the double eccentric arrangement 38, the mark 118 is useful as a zero reference so that small translatory motions can be employed when desired such as at the initiation of therapy. In a practical apparatus, the major eccentric 106 would have a diameter of approximately 13/16 inch with the diameter of the minor eccentric 112 being approximately 7/16 inch. Once the mark 116 on the minor eccentric 112 is positioned relative to the marks 118 through 128 or the major eccentric 106 as desired, a set screw 130 is employed to fix the eccentrics 106 and 112 relative to each other, thereby providing a desired "throw" or degree of motion for a given progression of therapy. Once the double eccentric arrangement 38 is set, the drive bar 40 is placed thereover such that the major eccentric 106 is received within the cutout 104 in the drive bar 40, a set screw then being used to fix the double eccentric arrangement 38 to the drive bar 40 and to that stucture associated with the drive bar 40.

The shaft 36 extends from the double eccentric arrangement 38 and into reduction gearbox 30 for connection to the 100-tooth gear 34 as aforesaid. The shaft 36 terminates in this connection to the gear 34. The gear 34 is directly driven through the 25-tooth gear 32 by means of the shaft 28 which extends into the reduction gearbox 30 from the joint 26. As is conventional with reduction gearbox structures, the interior of the box 30 is conveniently lubricated in order to facilitate smooth operation of the apparatus.

In the embodiments of the invention shown herein, the plates 42 and 48 are shown as being of the same size. In the embodiment of FIGS. 6–14, the stationary bar 50 can be adjusted as aforesaid and a certain amount of jaw discrepancy can thus be accommodated through the adjustment mechanisms provided as functional portions of the stationary bar 50. However, certain conditions such as Class 2 and Class 3 malocclusions can require longer plates. In a Class 2 malocclusion, commonly known as retrognathia, the leg portion of the plate 48 would be made longer in order to accommodate the "bite" of a retrognathic patient since such as patient has the lower jaw or mandible located further back than is typical. A Class 3 malocclusion, commonly known as prognathia, is characterized by having the lower jaw more forward than is typical. Accordingly, the leg of the plate 42 can be made longer to accommodate such a patient.

Figure 15:
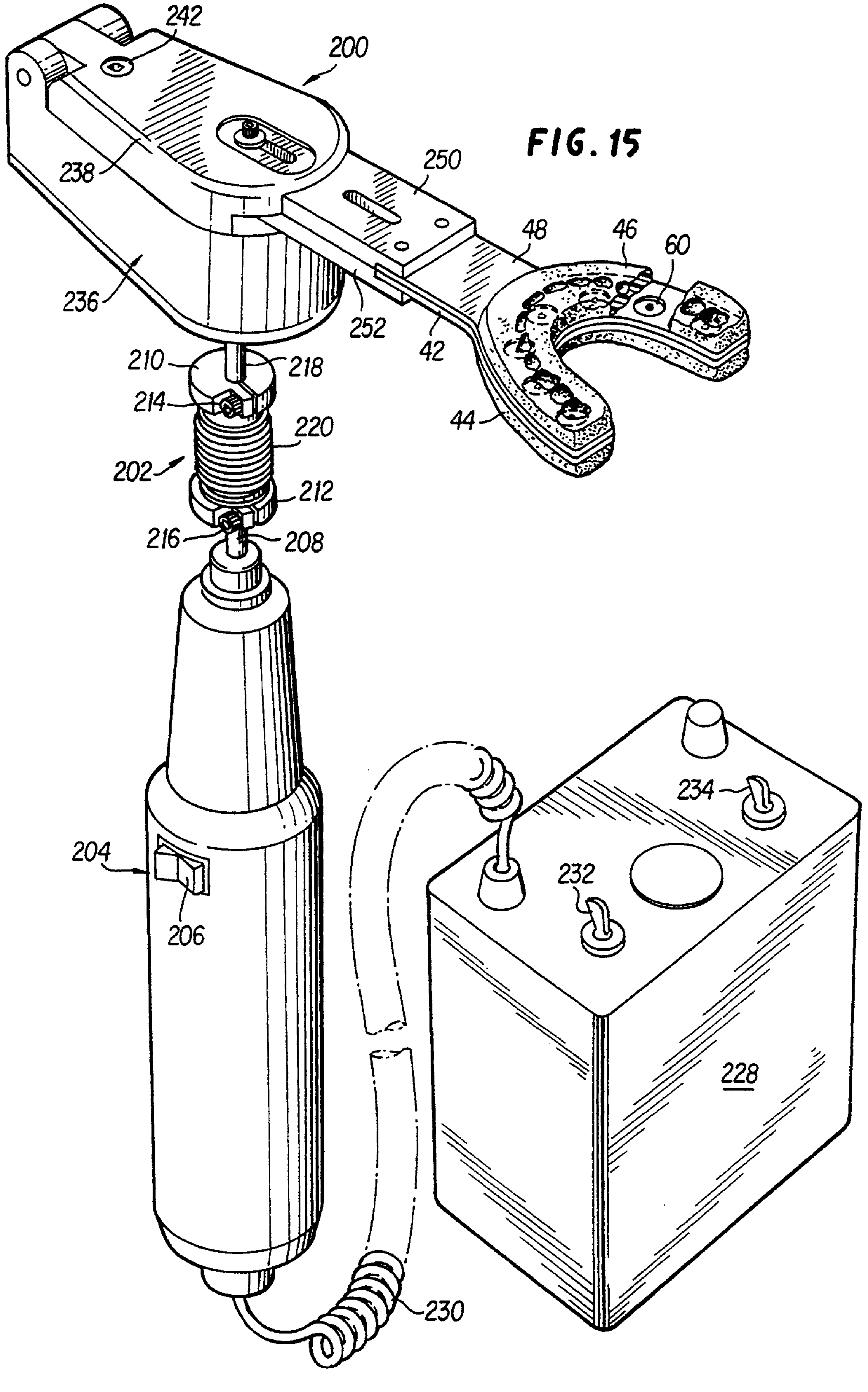
FIG. 15 is a perspective view of a second embodiment of the apparatus of the invention shown in a systems arrangement wherein a power source is separate from the graspable portion of the system.

Referring now to FIG. 15, another embodiment of the invention is seen to be comprised of a translatory drive unit 200 oppositely connected by means of a bellows joint 202 to a motor unit 204 having a motor (not shown) disposed internally of said unit 204 and operable by means of switch 206 in a manner similar to that described relative to the embodiment of FIGS. 6 through 14. The motor unit 204 drives shaft 208 which then drives the translatory drive unit 200 through the bellows joint 202. The bellows joint 202 is of substantially conventional structure and comprises upper and lower mounting collars 210 and 212, the collars being tightenable by means of tangentially oriented machine screws 214 and 216 respectively. The screws 214 and 216 are tightened to positively hold the bellows joint 202 to the shaft 208 and shaft 218 exiting the translatory drive unit 200. Bellows 220 of the bellow joint 202 connect in a conventional fashion to the upper and lower mounting collars 210 and 212 to provide a universal joint which is essentially similar in function to the joint 26 described above. As can be inferred from the foregoing disclosure, the shaft 218 exiting the translatory drive unit 200 joins to the bellows joint 202 and is positively affixed thereto by means of the upper mounting collar 210 as tightened by the screw 214. Similarly, the shaft 208 extending from the motor unit 204 joins to the bellows joint 202 by means of the lower mounting collar 212 as tightened by the screw 216. The function of the bellows joint 202 is to provide "give" or flexibility so that the user of the apparatus of FIG. 15 is not required to maintain the apparatus in a strictly maintained relation with the mouth. The universal joint 26 of FIG. 6 functions similarly but is formed of upper and lower plates 222 and 224 respectively having holes disposed about the periphery of said plates 222, 224 through which rod-like connecting elements 226 extend (as seen in FIG. 6). The universal joint 26 is conventional in function such that the lower plate 224 can skew relative to the stationary upper plate 222 to provide a desired freedom of motion. It should be understood that the bellows joint 202 and universal joint 26 can be used interchangeably with either joint being functional with the unit 12 or with the apparatus of FIG. 15 as well as other apparatus described herein.

Still referring to FIG. 15, a battery pack 228 is connected to the motor unit 204 by means of an insulated cord 230. The battery pack 228 is intended to be positioned remotely from the translatory drive unit 200/motor unit 204 and can be rechargeable as is conventional. The battery pack 228 could be worn on the user by means of straps or belts (not shown) in a manner which facilitates portable use of the apparatus of FIG. 15. A console (not shown) can replace the battery pack 228 and can be used to convert AC wall power to DC current. Such a console would be connected to the motor unit 204 by means of an insulated cord such as the cord 230. The console would be remotely located relative to the motor unit 204 and the drive unit 200 and would conveniently be located on a desk or similar horizontal work surface. Flexible cable drive is also possible.

The motor unit 204 can be shaped to facilitate being grasped by a user so that a user can hold the motor unit 204 while using the apparatus. The motor unit 204 can contain a biplanetary gear reduction system (not shown) which facilitates gearing down of the translatory drive unit 200 to a desired unit speed. The battery pack 228 can include a toggle switch 232 for controlling forward and reverse and a toggle switch 234 for power actuation. The battery pack 228 can also be provided with a rheostat (not shown) which enables a selection of a range of revolutions per minute for the output of the translatory drive unit 200. Although not shown in FIG. 15, the motor unit 204 can be configured to include a pistol grip or other grip so that the unit 204 can be readily grasped by a user.

The translatory drive unit 200 can be further seen in FIGS. 16 through 26 to comprise a casing 236 and a clam shell plate 238 hingedly mounted to said casing 236 by means of hinge arrangement 240. The casing 236 and clam shell plate 238 form the main body of the translatory drive unit 200, the casing 236 further serving to enclose a series of gears as will be described hereinafter. The casing 236 and clam shell plate 238 are preferably formed of hardened anodized aluminum and are shaped with arcuate portions both for convenience and appearance. The plate 238 is formed with an aperture 242 which aligns with a threaded bore 244 formed in upper planar surface 246, the aperture 242 and the bore 244 being located anteriorly of the unit 200 near the hinge arrangement 240. A screw 248 (shown best in FIG. 21) is received within the aperture 242 and threaded bore 244 and acts to positively hold the clam shell plate 238 to the casing 236 when the screw 248 is tightened.

The clam shell plate 238 fixedly mounts upper bar 250, the bar 250 mounting the yoke-shaped plate 48 which is identical to the plate 48 described relative to the embodiment of FIGS. 6 through 14. The plate 48 of FIG. 16 inter alia also mounts registration 46 in a manner exactly as described thereinabove relative to the embodiment of FIGS. 6 through 14.

Figure 16:
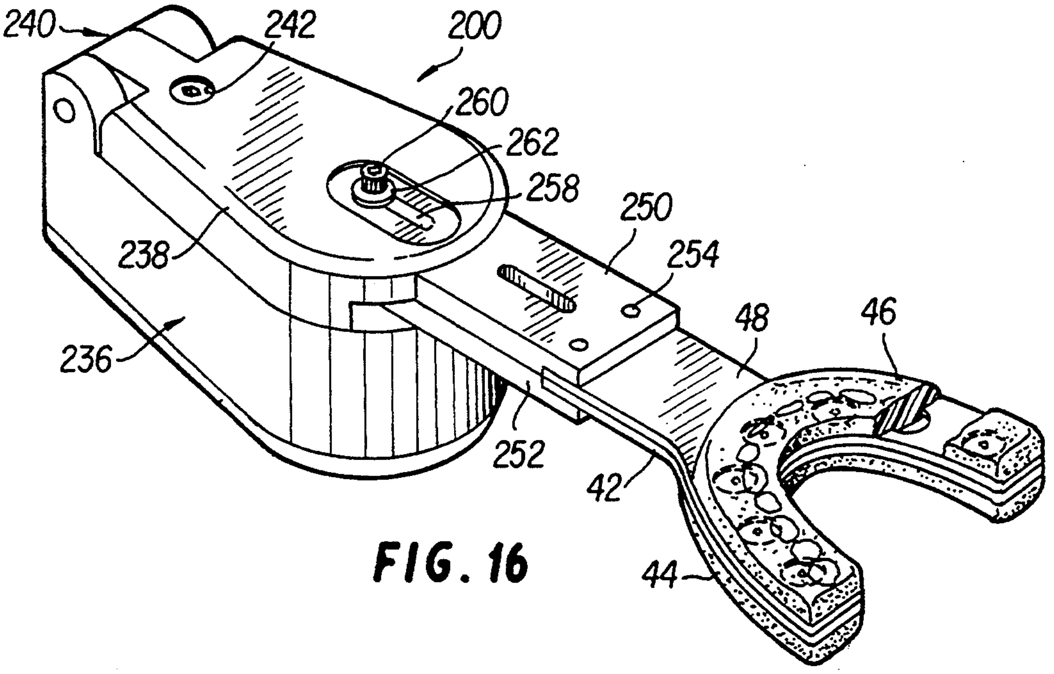
FIG. 16 is a perspective view of a second embodiment of the invention.
Figure 17:
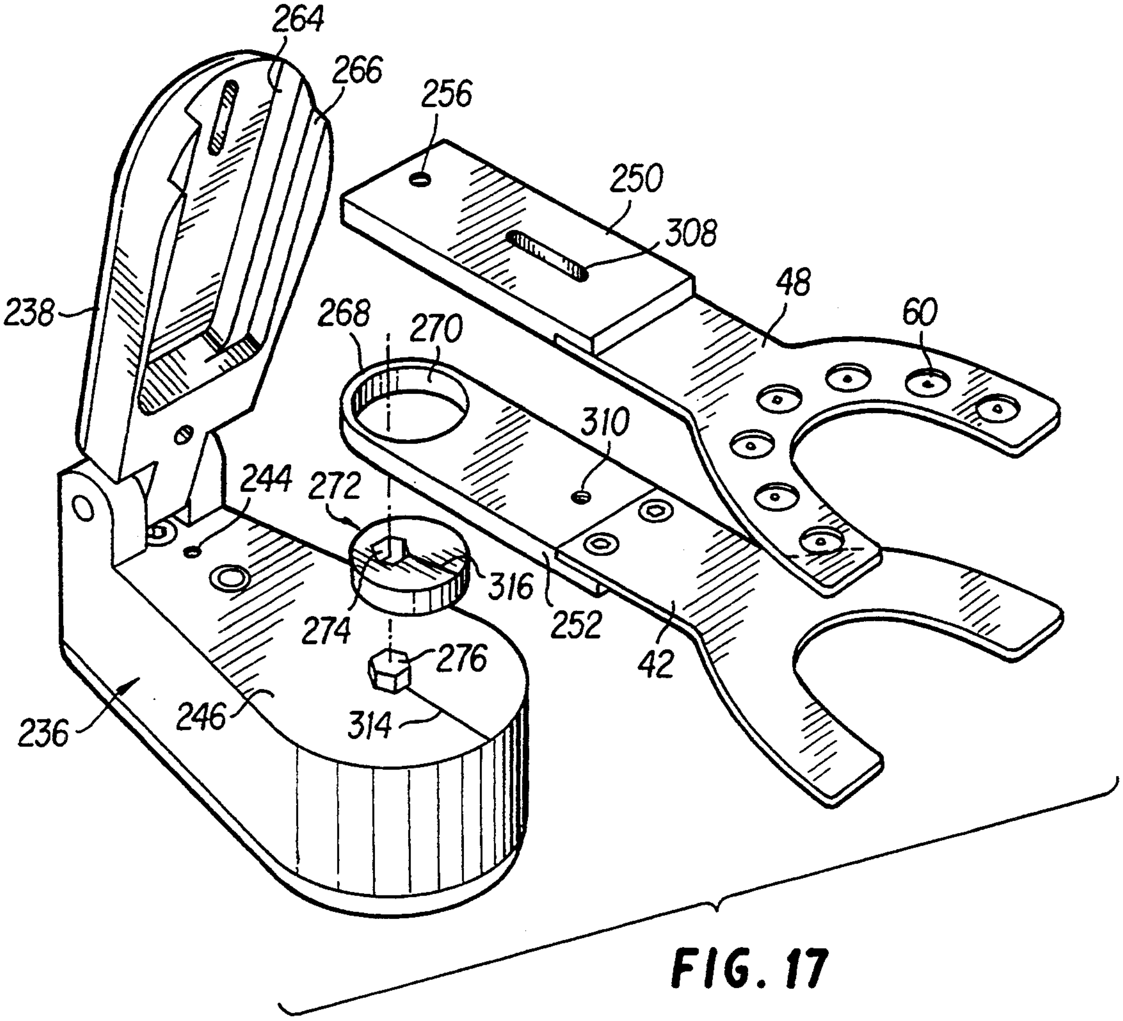
FIG. 17 is an exploded view of the apparatus of FIG. 16 with the apparatus opened to illustrate the plate arrangement.
Figure 18:
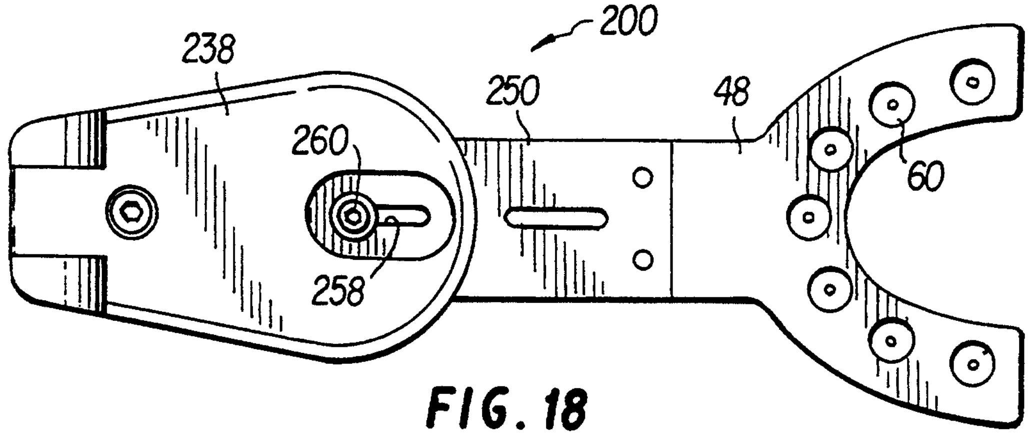
FIG. 18 is a plan view of the apparatus of FIG. 16.
Figure 21:
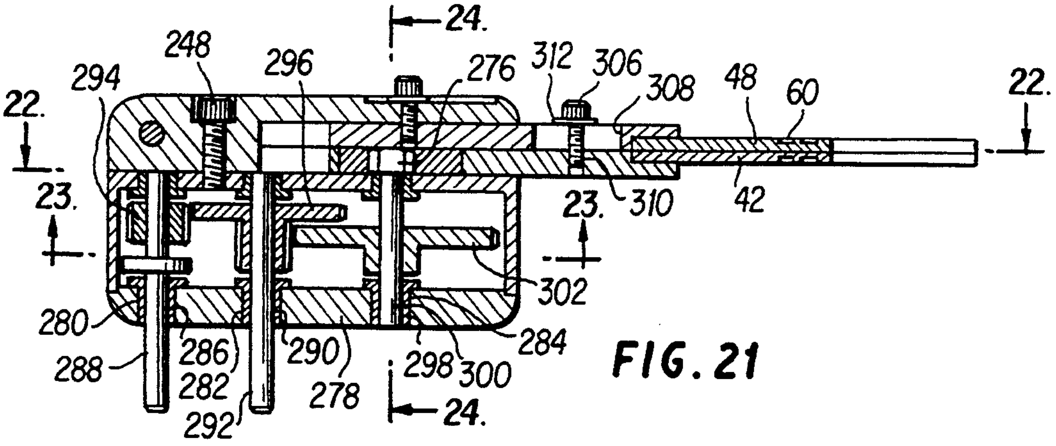
FIG. 21 is a side elevational view in partial section of the apparatus of FIG. 16.
Figure 22:
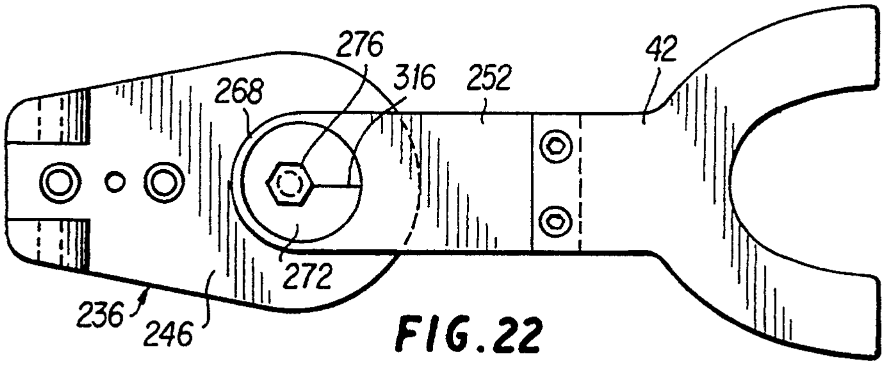
FIG. 22 is a sectional view taken along lines 22—22 of FIG. 21.

As best seen in FIGS. 17 and 21 inter alia, a drive bar 252 is mounted for movement relative to the surface 246 of the casing 236 as will be described hereinafter, the drive bar 252 mounting the yoke-shaped plate 42 which bears registration 44. The plate 42 and registration 44 of FIG. 16 are preferably identical to the corresponding structure of the embodiment of FIGS. 6 through 14. Further, the registrations 44 and 46 are mounted to the plates 42 and 48 respectively according to the procedures described above. The plates 42 and 48 are preferably formed of a plastic material such that said plates can be discarded along with the registrations 44 and 46 after use of the unit 200. The plates 42 and 48 are mounted, preferably removably, to the bars 252 and 250 respectively by means of screws 254.

The stationary upper bar 250 has a threaded bore 256 capable of aligning with any portion of a slot 258 formed in the clam shell plate 238. Accordingly, a screw 260 can be utilized in combination with a washer 262 to mount the stationary upper bar 250 to the clam shell plate 238. As can be readily seen in the drawings, the screw 260 is received within the slot 258 along any portion of said slot with the stationary upper bar 250 being moved in a longitudinal sense to align the threaded bore 256 with a desired portion of the slot 258 such that the screw 260 can be received through the slot and into the threaded bore 256. Tightening of the screw 260 causes the upper stationary bar 250 and thus the plate 48 to be mounted stationarily relative to the clam shell plate 258. Through use of the slot 258 formed in the clam shell plate 238, the location of the plate 48 can be adjusted "forwardly" or "backwardly" in order to provide a desired range of adjustment for the plate 48.

As is clearly seen in FIG. 17 inter alia, the stationary upper bar 250 is received within an inset 264 formed in the clam shell plate 238. A larger inset 266 is formed below the inset 264 in the clam shell plate 238, the inset 266 receiving the drive bar 252. The drive bar 252 is formed with an arcuate rear portion 268 and has a circular aperture 270 formed in the anterior portion thereof, the aperture 270 receiving any one of a series of eccentric cams 272 (only one of the cams 272 being shown). Each of the cams 272 is formed with a six-sided aperture 274 for receiving a six-sided drive pin 276. The pin 276 is driven by means of a gear and shaft arrangement located internally of the casing 236 as will be described hereinafter. Rotation of the eccentric cam 272 by means of the drive pin 276 causes movement of the drive bar 252/plate 42/registration 44 to cause the mandible of a patient to be moved and thereby to move the condyle of the temporomandibular joint in a translatory motion. The selection of a particular eccentric cam 272 and the operation of the translatory drive unit 200 will be further described hereinafter after completion of a discussion of the remaining structure of the unit 200.

Figure 19:
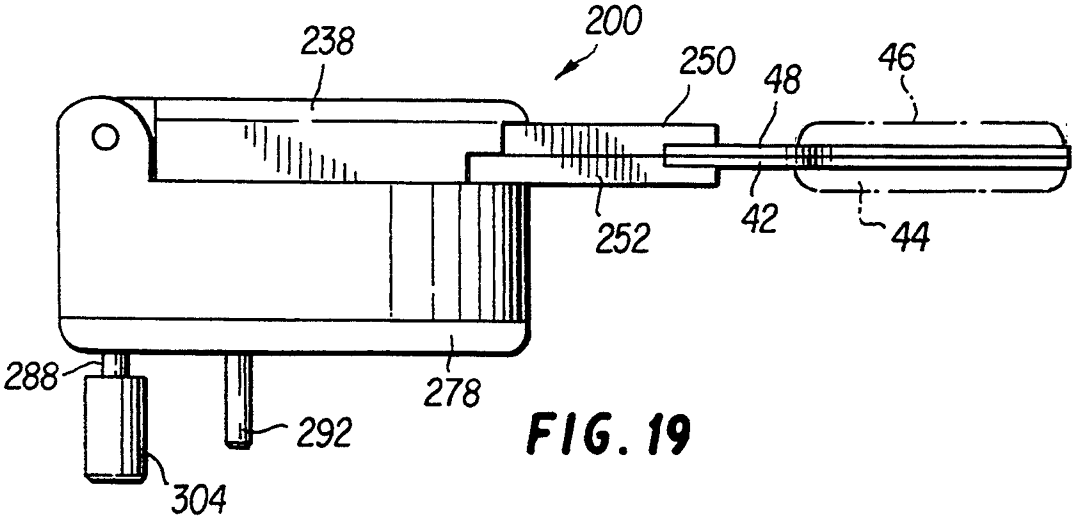
FIG. 19 is a side elevational view of the apparatus of FIG. 16.
Figure 20:
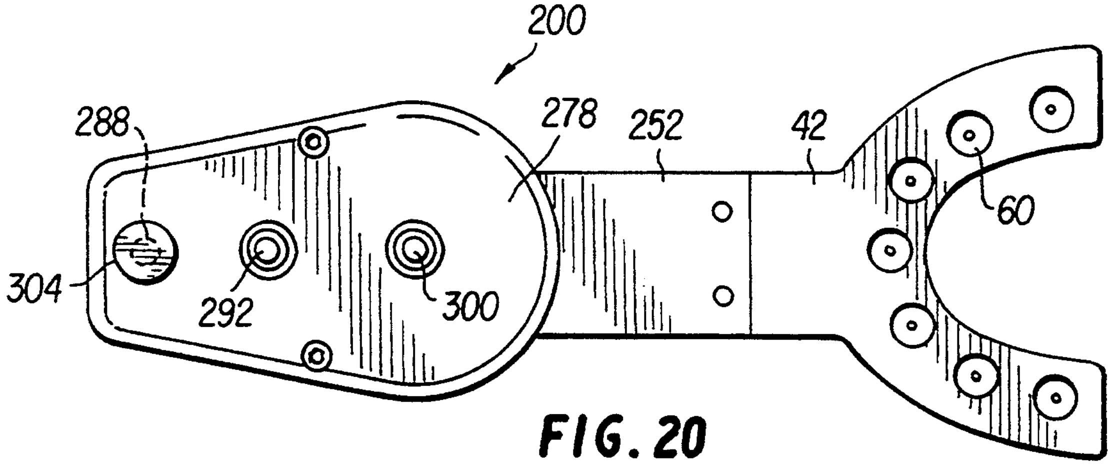
FIG. 20 is a view of the apparatus of FIG. 19 taken from the underside thereof.
Figure 23:
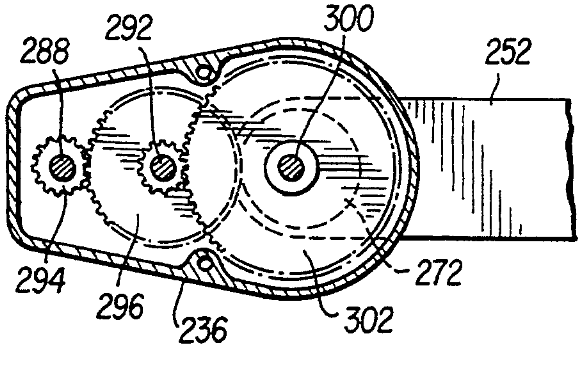
FIG. 23 is a sectional view taken along lines 23—23 of FIG. 21 and being partially cut away.
Figure 24:
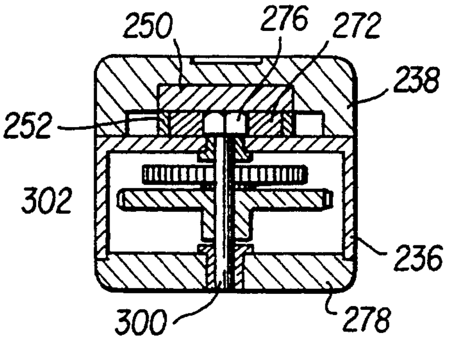
FIG. 24 is a sectional view taken along lines 24—24 of FIG. 21.
Figure 25:
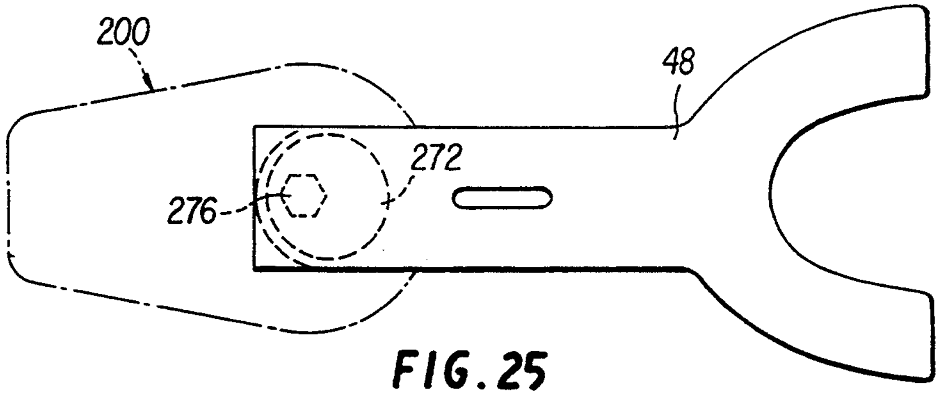
FIGS. 25, 26 and 27 are schematics illustrating the locations of the plates of the apparatus in several positions.
Figure 26:
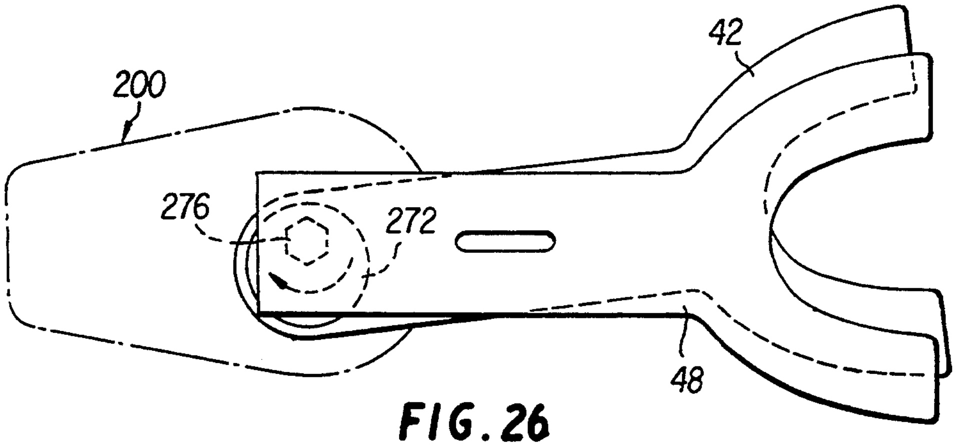

Referring now to FIGS. 19, 21 and 23 inter alia, the casing 236 is seen to comprise a bottom plate 278 having apertures 280, 282 and 284 formed therein. The aperture 280 receives a brass bushing 286 which mounts a reduced gear drive shaft 288. The aperture 282 receives a bushing 290 which mounts drive shaft 292. The drive shafts 288 and 292 extend externally of the casing 236 and, internally of the casing 236, the shafts 288 and 292 respectively mount gears 294 and 296. The aperture 284 receives bushing 298, the bushing 298 mounting shaft 300. The head of the shaft 300 comprises the six-sided drive pin 276 which extends externally of the casing 236 in surmounting relation to the planar surface 246 where said drive pin 276 receives a selected one of the plurality of eccentric cams 272 as noted above. The shaft 300 further mounts gear 302 within the interior of the casing 236. The gears 294, 296 and 302 form a gear reduction arrangement so that the six-sided drive pin 276 can be driven at a desired speed for rotation of one of the eccentric cams 272. A shaft coupling 304 as seen best in FIG. 19 can be received and held on to either one of the drive shafts 288 or 292 in order to provide desired gear reduction.

A set of the arcuate cams 272 preferably includes a total of fourteen of the cams 272 with each cam representing a one-half millimeter increment from ½ mm to 7 mm. Each eccentric cam 272 includes a six-sided aperture 270 which is located at varying distances from the center of the cams 272 in order to change the "throw" from ½ mm to 7 mm. The eccentric cam 272 which is mounted on the drive pin 276 at any given time causes motion to be transmitted from the motor unit 204 to the plate 42 and thus the registration 44 to transfer translatory motion to the condyles of the joints on either side of the mandible. Drive through the shaft 288 results in a lower rotational output of the shaft 300 for a given RPM of the motor unit 204 as compared to driving of the shaft 292 which produces a higher rotational output from the given input of the motor unit 204.

As can be seen in FIG. 21, a screw 306 is received within slot 308 formed longitudinally in the upper bar 250. The drive bar 252 has an alignable threaded bore 310 formed therein which receives the distal end of the screw 306. The screw 306 can receive a washer 312 to provide a more positive mounting of the bars 250 and 252 together. Use of the screw 306 to mount the bars 250, 252 together is for the purpose of forming the registrations 44 and 46 on the plates 42 and 48 respectively as has previously been described. The screw 306 is only used in taking impressions on the plates 42 and 48 and is not utilized during operation of the apparatus to impart translatory motion to the temporomandibular joint. The length of the slot 308 is chosen in order to allow adjustment of the plates 42 and 48 relative to each other to accommodate differing positions of the upper jaw and mandible as occurs between individual patients. The screw 306 is not left in place on assembly of the plates 42/48 to the unit 200, this assembly being shown in FIG. 21 solely for the purpose of illustration.

Referring now particularly to FIG. 17, an index line 314 is seen to be drawn on the distal portion of the surface 246, the index line extending substantially along a longitudinally oriented line of symmetry of the surface 246. Each of the eccentric cams 272 is provided with an index line 316. The two index lines 315 and 316 essentially extend from forwardmost corners of the six-sided drive pin 276 and six-sided aperture 274 respectively. The index lines 314 and 316 are aligned with each other when each of the eccentric cams 272 is mounted on the drive pin 276. Care must be taken that the drive bar 252 is at its most posterior limit when mounting the cams 272. At that posterior limit, the bars 250, 252 having the plates 48 and 42 mounted thereto respectively are mounted to the casing 236/clam shell plate 238. The registrations 44 and 46 are then secured within the mouth of the patient and the upper stationary bar 250 is firmly tightened to the clam shell plate 238 as aforesaid with the index lines 314 and 316 being aligned. In this manner, all movement will be forward of centric occlusion.

Figure 28A:
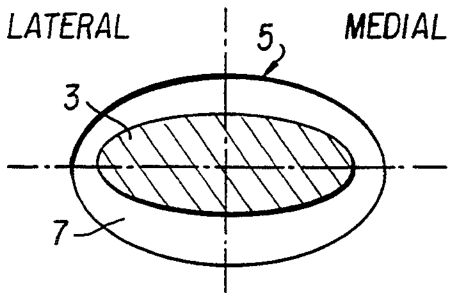
FIGS. 28A, 28B, 28C, 28D and 28E are schematics illustrating the location of the condyle within the temporomandibular joint on movement occasioned by clockwise motion of the apparatus of the invention.
Figure 28B:
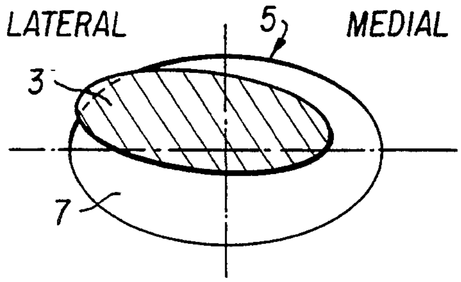
Figure 28C:
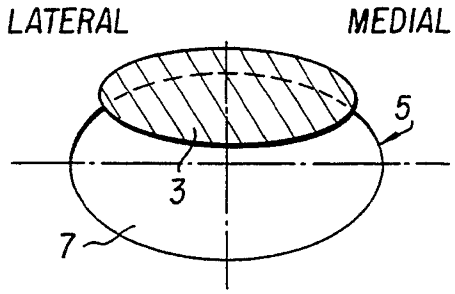
Figure 28E:
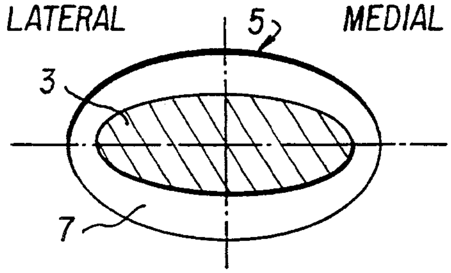

In operation, the several embodiments of the apparatus function in a similar manner to translate the temporomandibular joint. As is seen in FIGS. **28*a* through 28*e* and 29*a* through 29*e*, the movement of the condyle in the fossa is shown. FIGS. 28*a* through 28*e* illustrate clockwise turning of the drive pin 276 to cause the right joint to move in the manner shown. Counter-clockwise movement is seen in FIGS. 29*a* through 29*e*. Referring particularly to FIGS. 28*a* through 28*e*, the lateral and medial references are indicated in each of the figures. In FIG. 28*a*, the condyle 3 is seen to be in a neutral position relative to the articular eminence 5. In FIG. 28*b*, the condyle 3 has moved laterally and rotated slightly anteriorly according to the motion provided by the apparatus and methodology of the invention. In FIG. 28*c*, the condyle 3 has moved forward, toward, to or past the articular eminence 5. On the backward stroke as seen in 28*d*, the condyle 3 has moved medially and the lateral pole has rotated slightly posteriorly. FIG. 28*e*** illustrates return of the condyle to a neutral position.

Figure 29A:
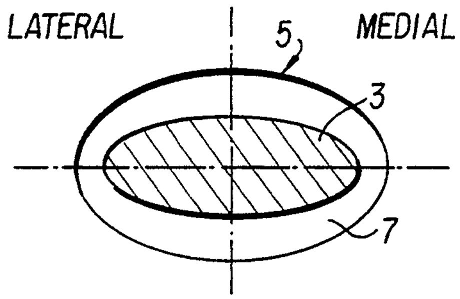
FIGS. 29A, 29B, 29C, 29D and 29E are schematics illustrating the location of the condyle within the temporomandibular joint on movement occasioned by counter-clockwise motion of the apparatus of the invention.
Figure 29B:
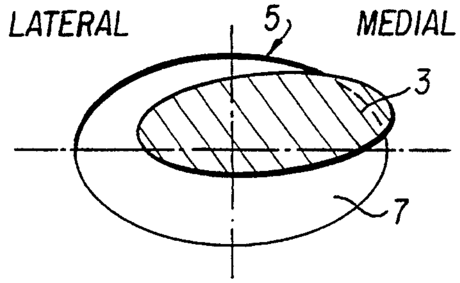
Figure 29C:
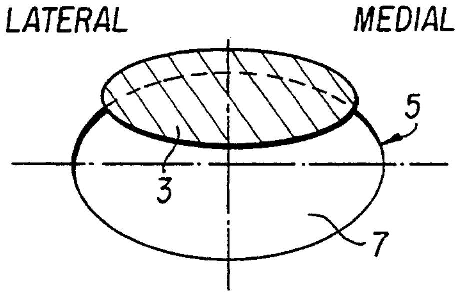
Figure 28D:
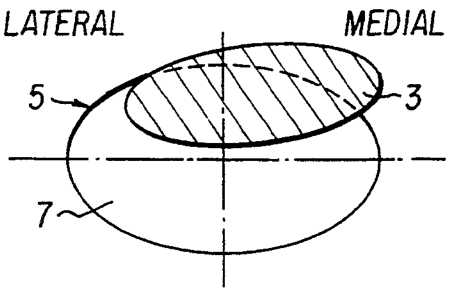
Figure 29D:
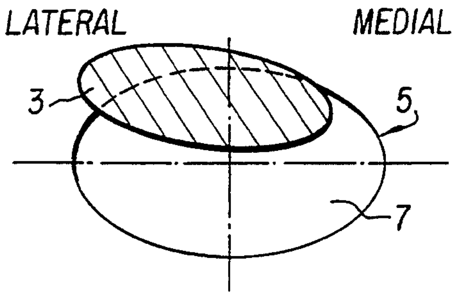
Figure 29E:
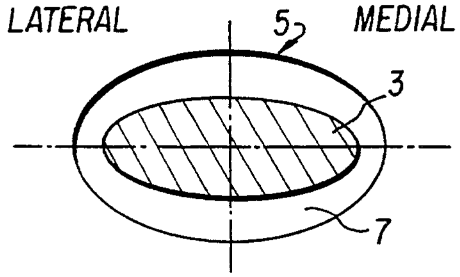

Considering now FIGS. **29*a* through 29*e*, counter-clockwise turning of the drive pin 276 causes the motion of the condyle 3 as seen in the figures. The condyle 3 is seen to be in a neutral position in the fossa 7 as seen in FIG. 29*a*. FIG. 29*b* shows the condyle 3 to have moved medially with the medial pole rotating slightly anteriorly. In FIG. 29*c*, the condyle 3 has moved toward, to or past the articular eminence 5. On the backward stroke as is shown in FIG. 29*d*, the condyle 3 has moved laterally with the medial pole rotating slightly posteriorly. FIG. 29*e* again shows the neutral position of the condyle 3**.

Figure 27:
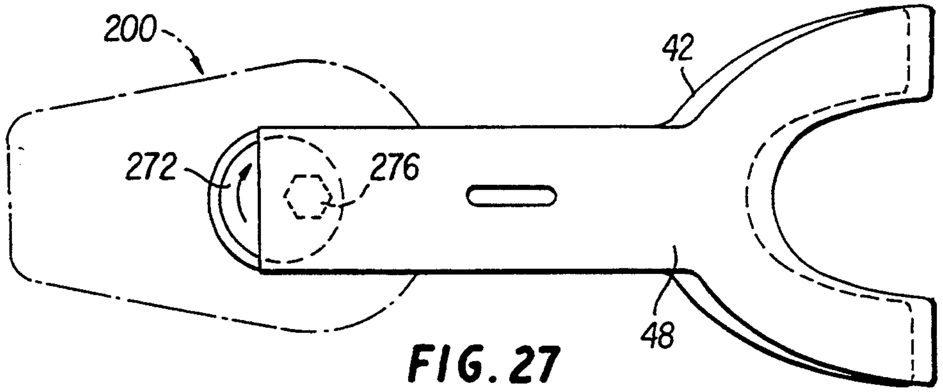

Referring once again to FIGS. 25, 26 and 27, the motion of the drive bar 252 and associated plate 42 during clockwise motion of the drive pin 276 is seen to cause the indicated movement of said plate 42. In essence, any point on the plate 42 effectively scribes out an oval on each rotation of the drive pin 276, this movement causing the temporomandibular joint on each side of the mandible to be moved in translation both continuously and passively for the purpose of rehabilitation of the temporomandibular joint as described herein.

Referring now to FIGS. 30 through 40, a third embodiment of the invention is shown to comprise apparatus 400 having a translatory drive unit 402 and a motor housing/handle 404. The apparatus 400 is similar in structure and operation to the two embodiments of the invention previously described in an explicit fashion relative to FIGS. 6 through 14 and 15 through 27 respectively. Many of the structural elements of the third embodiment of FIGS. 30 through 40 are very similar to or are essentially identical to corresponding structure described hereinabove relative to the first two embodiments of the apparatus of the invention. Having thus so indicated, reference will not be further made back to similar or identical structure and operation which is common to the third embodiment of FIGS. 30 through 40 and the previously described embodiments. Further notice is taken that certain structure present in the first two embodiments are not present in the embodiment of FIGS. 30 through 40, a particular feature being a universal joint structure coupling a handle element and a translatory drive unit. As is clearly seen in FIGS. 30 through 40, the translatory drive unit 402 is mounted in a fixed relation to the motor housing/handle 404.

Figure 30:
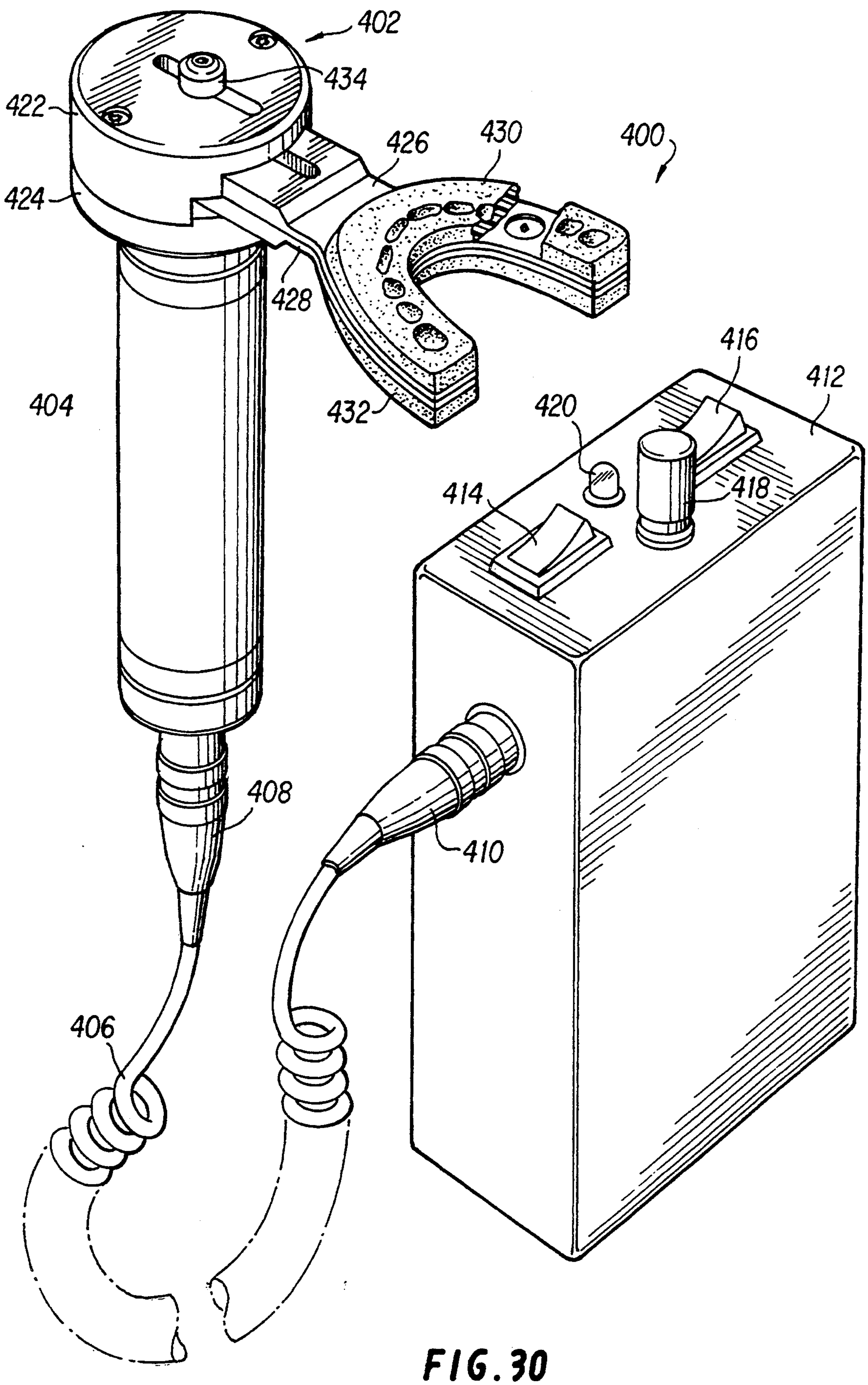
FIG. 30 is a perspective view of a third embodiment of the apparatus of the invention shown in a systems arrangement wherein a power source is separate from but electrically connected to the graspable portion of the system.

The motor housing/handle 404 essentially constitutes a visible casing which holds a motor (not shown) internally thereof, this casing being graspable by a user who holds the motor housing/handle 404 while the apparatus 400 is in use. The motor which is not shown can take the form of a number of conventional motors presently available and can contain gear reduction elements (not shown) which are of conventional construction. The motor contained within the motor housing/handle 404 is electrically connected through cord 406 and cable connections 408 and 410 respectively to control module 412. The cord 406 and cable connections 408 and 410 are of conventional construction and merely serve to connect the apparatus 400 to the control module 412 so that power can be applied to the motor (not shown) contained within the motor housing/handle 404 for operation of the translatory drive unit 402. Control is also effected through the control module 412 such as by means of on/off switch 414, forward/reverse switch 416 and speed selector 418. Control switch structure can also be provided on the apparatus 400 and particularly on the motor housing/handle 404 although such structure is not shown in the drawings related to this embodiment. The control module 412 essentially comprises a housing constructed of sufficiently strong plastic or other material and contains rechargeable batteries (not shown) which power the motor (not shown) contained within the motor housing/handle 404. It is to be understood that the control module 412 and associated switches and the like can be configured in a manner conventional in the art. The control module 412 is conveniently placed when in use in the patient's lap, on a horizontal surface or on a belt loop. The control module 412 can also be configured to contain a battery charger (not shown). Although also not shown in the drawings, the switches 414 and 416 as well as the speed selector 418 can be provided with light emitting diodes which indicate function. As is shown in FIG. 30, a light emitting diode or other luminaire is provided as a low battery warning light 420. The control module 412 can thus be formed as a portable unit or as a console unit intended for stationary operation on a table top or the like. While the apparatus 400 can be driven other than by the use of the control module 412, the module 412 is simple and convenient in structure and operation and is of particular utility in the providing of power through the use of rechargeable batteries (not shown) to drive the motor (not shown) contained within the motor housing/handle 404, which motor is conveniently taken to be driven by direct current as is provided by conventional rechargeable batteries.

The motor housing/handle 404 is shaped to facilitate grasping by a user so that a user can hold the motor housing/handle 404 while using the apparatus 400. The body of the motor housing/handle 404 can be knurled such as is conventional in the art in order to further facilitate grasping and retention in the hand by a user.

The translatory drive unit 402 is provided with upper and lower casings 422 and 424 respectively, these casings essentially enclosing most structure forming the translatory drive unit 402 with the very obvious exception of upper and lower plates 426 and 428 and the registrations 430 and 432 respectively formed on said plates. The lower casing 424 joins to the motor housing/handle 404 at the distal end thereof and is connected by means of fasteners which essentially join the lower casing 424 to the motor and speed reduction arrangement (if any) which are contained within the motor housing/handle 404 and which are not shown as aforesaid. The upper and lower casings 422 and 424 as well as the motor housing/handle 404 is preferably constructed of high grade anodized aluminum although other materials can conveniently be employed including materials generally referred to as plastics. It is to be understood that plastic or polymeric materials used in the construction of any portion of the apparatus 400 require a desired degree of rigidity, appropriate durometer, etc., with the exception of the registrations 430 and 432 which are preferably formed of curable acrylic materials or the like as is described herein.

The upper and lower plates 426 and 428 can be constructed of stainless steel/hard anodized aluminum or in the alternative can be formed of a rigid polymeric material such as a material manufactured by DuPont and known under the trademark of DELRIN. The plates 426 and 428 are intended for single patron use especially in view of the fact that the registrations 430 and 432 are custom fit to the plates 426 and 428 respectively for each individual patient who is to be treated with the apparatus 400. The formations of registrations such as the registrations 430 and 432 onto plates such as the upper and lower plates 426 and 428 have been described in detail relative to the previous embodiments of the invention. The shape of the plates 426 and 428 including yoke-shaped portions designed to fit the mouth have also been previously described relative to the other embodiments of the invention. It is to be seen that the upper plate 426 has a portion referred to as upper bar 436 while the lower plate 428 has a portion referred to as the drive bar 438, the upper bar 436 and the drive bar 438 being of increased thickness relative to the yoke portions of the plates 426 and 428 respectively. The upper bar 436 has a slot 444 and a threaded aperture 448 disposed anteriorly of the slot 444, the plates being loosely joined by screw 434 through slot 444 and threaded aperture 442 in the lower plate 428 when adjusting relative plate position for each patient prior to apparatus assembly (not shown). When assembled, threaded stem 433 of the screw 434 is received within threaded aperture 448 in the upper plate 426 with the shank portion of the screw 434 being received through the slot 435 in the upper casing 422.

Figure 31:
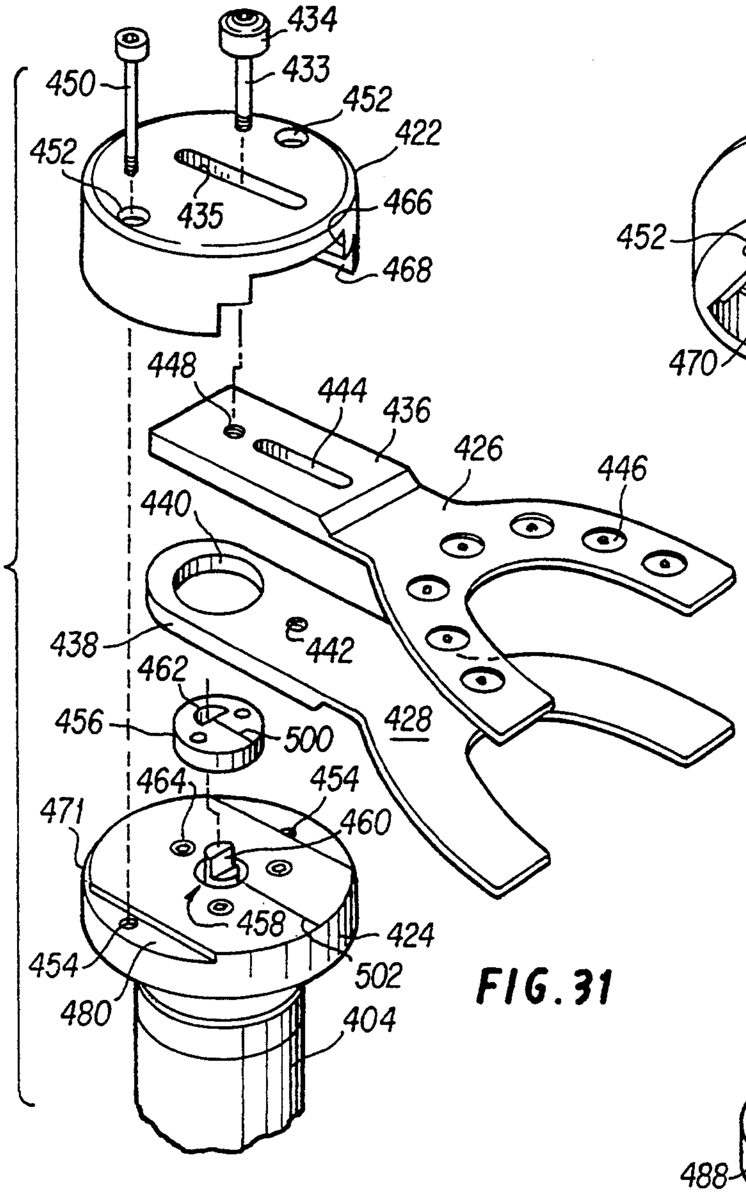
FIG. 31 is an exploded view of a portion of the third embodiment of the invention.
Figure 32:
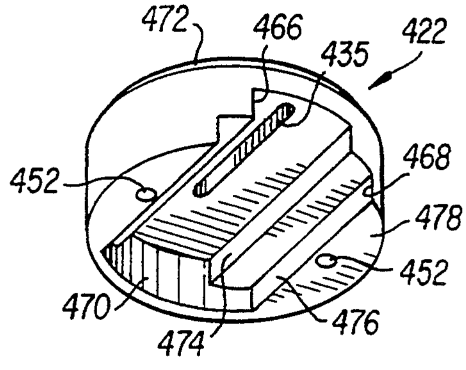
FIG. 32 is a perspective view of a portion of the casing of the third embodiment of the invention.
Figure 35:
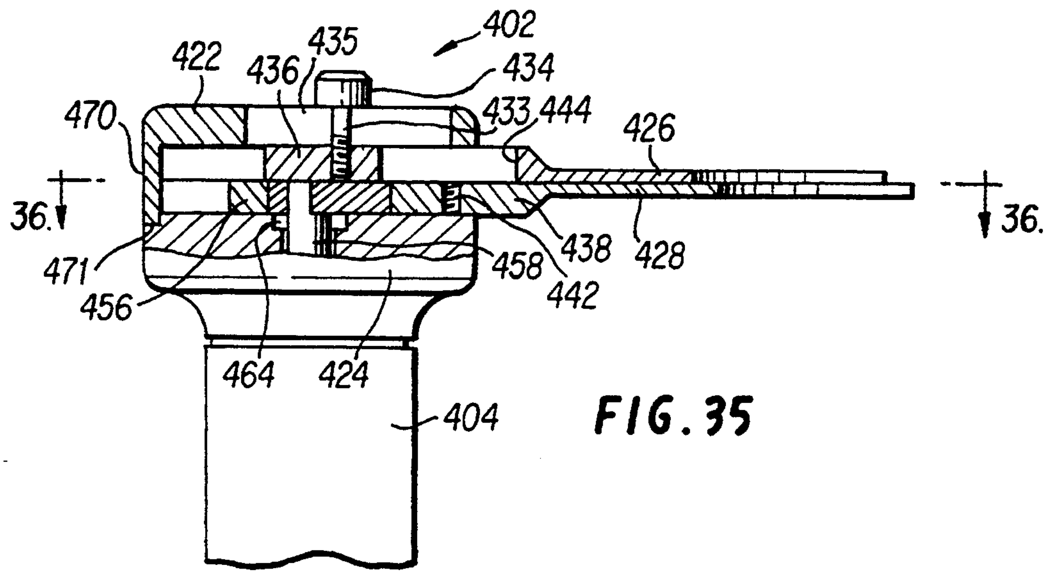
FIG. 35 is a side elevational view of the third embodiment of the invention.
Figure 36:
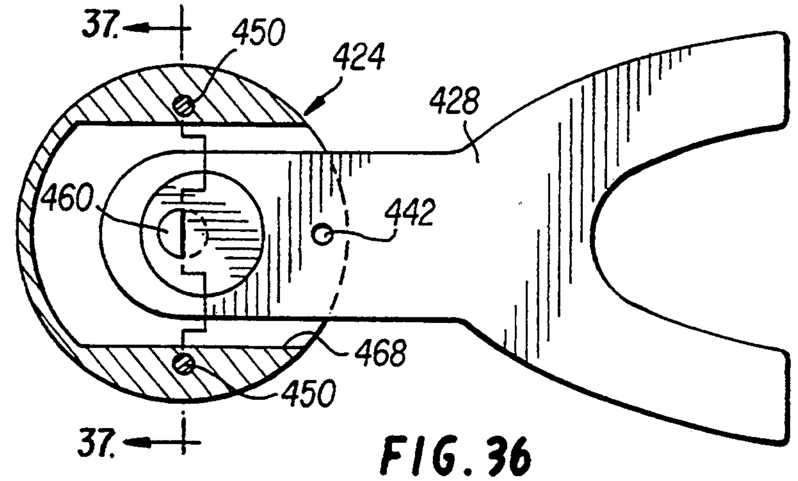
FIG. 36 is a plan view in partial section of the apparatus of FIG. 35 taken along lines 36—36.
Figure 37:
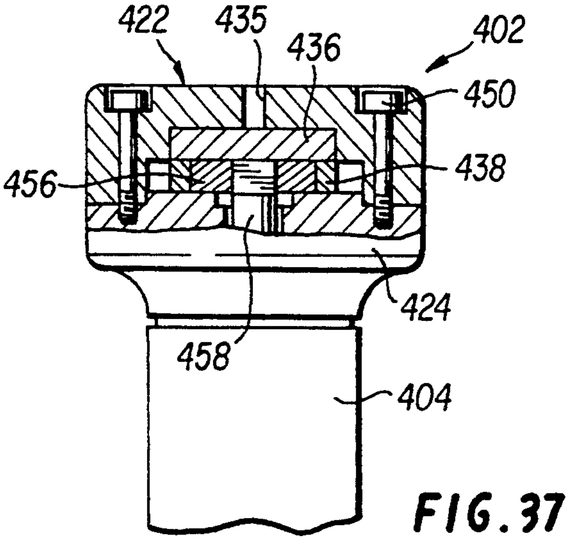
FIG. 37 is a side elevational view in partial section of the apparatus of FIG. 36 taken along lines 37—37; and, FIGS. 38, 39 and 40 are schematics illustrating the location of the plates of the apparatus in several positions.

The structure of the upper casing 422 can be seen particularly in FIGS. 31 and 32 as well as in FIGS. 35 and 37. Referring also to these figures inter alia, the manner by which the upper plate 426 is fitted to the upper casing 422 can be appreciated. The upper bar 436 is seen to be received within the upper bar cut out 466 formed in the upper casing 422, the cut out 466 surmounts drive bar cut out 468 through which the lower plate 428 and particularly the drive bar 438 of said plate 428 extends. The upper casing 422 further comprises a rear wall 470 which engages ledge 471 formed in the lower casing 424 as best seen in FIGS. 31 and 35. The upper bar 36 of the upper plate 426 is seen to be received between upper shoulders 474 formed in the shaped recess portions of the upper casing 422, the upper bar 436 fitting substantially flushly with the upper shoulders 474. Lower shoulders 476 formed in the upper casing 422 are more widely spaced apart than are the upper shoulders 474 and receive the drive bar 438 of the lower plate 428 for motion therewithin. Chord shoulders 478 which are planar portions disposed diametrically oppositely apart on the under side of the upper casing 424 and cooperate with the rear wall 470 on the upper casing 422 and the ledge 471 on the lower casing 424 to cause the upper and lower casings 422 and 424 to fit together only one way. Upper perimetrical portions of the upper casing 422 can be beveled at 472 to provide a pleasing appearance and to avoid sharp edges.

The upper casing 422 is provided with threaded apertures 452 which extend through the chord shoulders 478 and align with threaded apertures 454 formed in the chord cut outs 480 of the lower casing 424. Threaded screws 450 (only on screw 450 being shown in FIG. 31) are received within the apertures 452 and 454 to hold the upper and lower casings 22 together. It will readily be understood that the apertures 452 need not be threaded as desired.

The plates 426 and 428 are joined together loosely as aforesaid and fitted for a patient's occlusion, the slot 444 only being used for this purpose. The shank of the screw 434 would be essentially centered in the slot 444 for Class. I skeletal discrepancy, forward in slot 444 for Class II and rearward in slot 44 for Class III. After adjustment, the upper plate 426 is is secured to the upper casing 422 and the lower plate 428 is engaged with the drive portions of the apparatus 400 as described hereinafter.

Completing the description of the upper plate 426, it is to be seen that the yoke-shaped portion of the upper plate 426 which is received into the mouth of the user is provided with depressions 446 which facilitate holding of the registration 430 (shown best in FIG. 30) as has been previously described relative to essentially identical structure utilized in embodiments of the invention previously described. The under side of the yoke-shaped portion of the lower plate 28 is also provided with the depressions 446 for mounting of the registration 432.

Figure 33A:
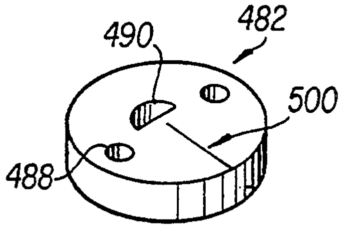
FIGS. 33*a*, 33*b* and 33*c* are perspective views of examples of eccentric cams used in the third embodiment of the invention.
Figure 33B:
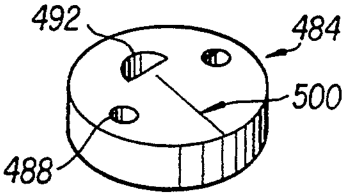
Figure 33C:
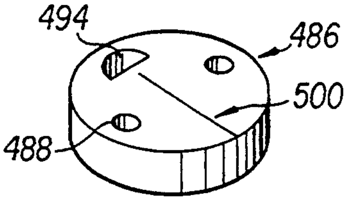
Figure 34:
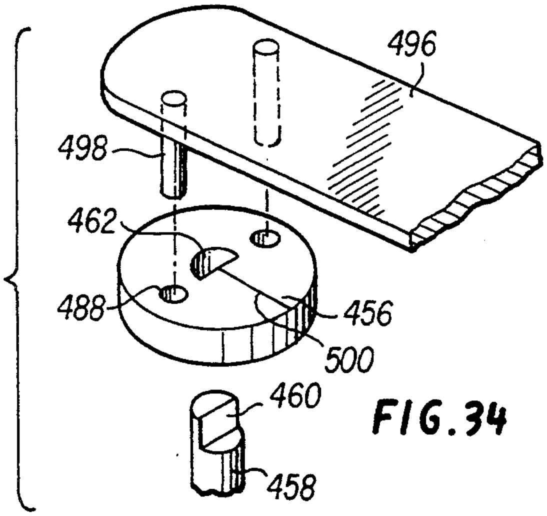
FIG. 34 is a perspective view of a tool used to adjust the position of one of the cams of FIG. 33 on the drive shaft of the third embodiment of the invention.

In the anterior end of the lower plate 428 a cam aperture 440 is formed, this aperture being circular in conformation (as seen in this embodiment), the cam aperture 440 receiving any one of a series of eccentric cams such as the cam 456 as is seen in FIG. 31. Eccentric cams 482, 484 and 486 are shown in FIGS. 33*a*, 33*b* and 33*c* respectively and will be described hereinafter relative to the degree of motion which is imparted by said eccentric cams as determined by a selection of the cams. As is the case with the cams 482, 484 and 486, the eccentric cam 456 is provided with a half-moon aperture 462 which receives half-moon stem 460 of drive shaft 458. The drive shaft 458 extends through the lower casing 424 centrally thereof to connect the eccentric cam 456 to the motor (not shown) held within the motor housing/handle 404. The drive shaft 458 is driven in a rotary motion which rotates the eccentric cam 456. Since the eccentric cam 456 is received within the cam aperture 440 formed in the drive bar 438 of the lower plate 428, the lower plate 428 is caused to move in a manner which imparts translatory motion to the lower jaw of a user of the apparatus 400 and in a manner such as has been previously described herein. As has also been described herein, the registration 430 is received in the upper jaw of a user whereas the registration 432 is received by the teeth or structures of the lower jaw. Since the upper plate 426 remains substantially stationary during operation of the apparatus 400, the lower plate 428 moves relative to the upper plate 426 to impart translatory motion to the lower jaw of a user.

Completing the structure of the lower casing 424, it is seen that screws 464 can be utilized to fasten the lower casing 424 to motor and/or gear reduction structure (not shown) held within the motor housing/handle 404 and which may extend into lower portions of the lower casing 424.

Referring now to FIGS. 31, 33*a* through 33*c* and 34 in particular, it is to be seen that the eccentric cams 456, 482, 484 and 486 are all provided with alignment tool engagement apertures 488 which are placed one each on either side of the half-moon aperture 462 formed in each eccentric cam respectively, the apertures 488 essentially lie along a diameter of the substantially circular cams. The cams can be formed of bronze/stainless steel and a set of ten cams is typically provided with the apparatus 400. These cams are incrementally graduated from ½ mm to 5 mm in a preferred use of the apparatus 400. Although not shown in the drawings, each cam is marked by millimeter increment which indicates the degree of motion or "throw" provided by each of the cams. Each cam is also provided with an index line 500 which essentially constitutes a scribed line on the upper surface of the cam. The index line 500 on each cam is aligned with a scribed line 502 formed on an upper surface of the lower casing 424 such that the index line 500 and the scribedline 502 can be aligned to set the apparatus 400 to an initial position. An alignment tool 496 having alignment pins 498 is utilized to align one of the eccentric cams, such as the cam 456 in FIG. 34. The alignment pins 498 are received within the alignment tool engagement apertures 488 and the alignment tool 496 is then manually manipulated such that the index line 500 aligns with the scribed line 502 as aforesaid. Alignment of the index line 500 and the scribed line 502 ensures that the cam 456 (or any of the other cams) is in its most backward position with all subsequent movement being forward of centric occlusion.

The eccentric cams 482, 484 and 486 are respectively provided with half-moon apertures 490, 492 and 494. While the apertures 462, 490, 492 and 494 could be chosen to assume other shapes which would allow driving by means of the drive shaft 458, the half-moon shape has been chosen for illustrative convenience in the description of this embodiment of the invention. Of particular importance in this situation is the location of the apertures 462, 490, 492 and 494. As will be noted in FIGS. 31 and 34, the aperture 462 is almost located along the diameter of the cam 456 extending through the alignment tool engagement apertures 488. The eccentric cam 456 thus provides only a small degree of translatory motion. As the apertures 490, 492 and 494 extend further toward the periphery of the cams 482, 484 and 486 respectively, it is to be seen that a greater degree of translatory motion is imparted to the lower jaw of a user by means of the motion imparted to the lower plate 428.

Figure 38:
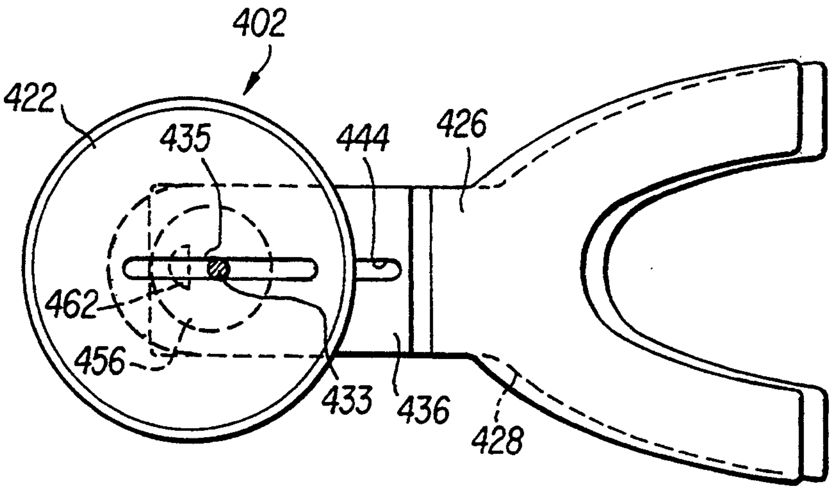
Figure 39:
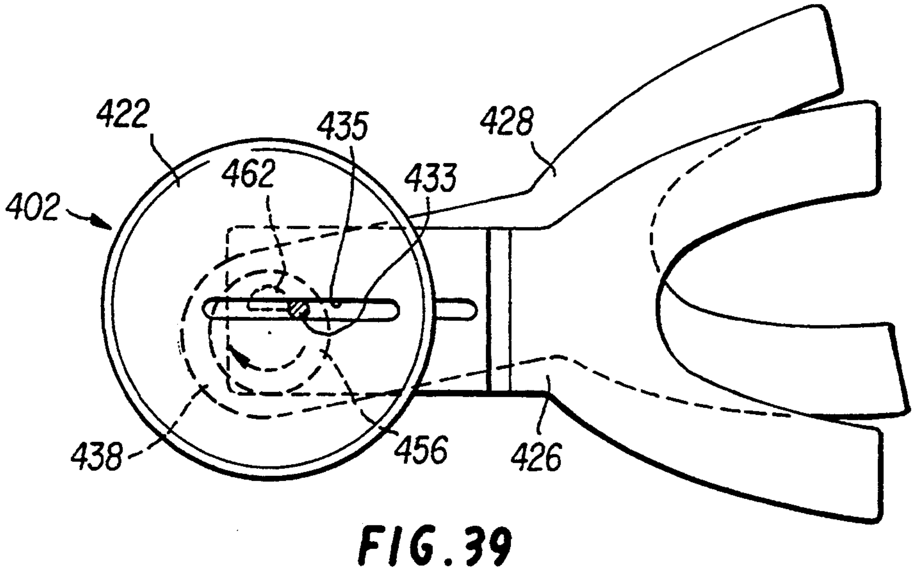
Figure 40:
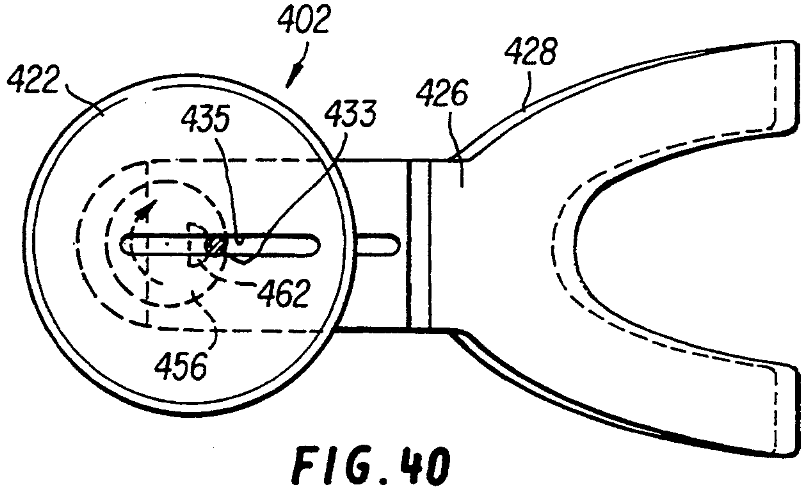

As can be seen in FIGS. 38, 39 and 40, the position of the lower plate 428 on rotation of the eccentric cam 456 can be seen. In these figures, the eccentric cam 456 is rotated through one-half of a revolution by the drive shaft 458 thereby causing distal portions of the lower plate 428 (which bear the registration 432) to move from an initial position to the greatest extent to one side at a quarter turn, as seen in FIG. 39, and then to its most inward position at one-half turn. It can then be seen from the motion illustrated in FIGS. 38 through 40 that the fullest lateral extent on the opposite side of the lower plate 428 occurs at ¾ turn with the initial position being returned to at a full 360° revolution of the eccentric cam of the drive shaft 458.

The following case histories are exemplary of treatment procedures and results obtained through practice of the present method and using apparatus configured according to the invention.

EXAMPLE I

A 43 year old female with a four year history of bilateral temporomandibular joint pain and severe headaches clinically associated with temporomandibular joint dysfunction. Previous therapy consisted of a series of intra oral splints, physical therapy, medication and bilateral arthroscopy undertaken approximately two years previous. Patient's chief complaint was severe bilateral temporomandibular joint pain and limited range of motion. Diagnosis was bilateral internal derangement with bilateral fibrous ankylosis, secondary to arthroscopy. Patient underwent bilateral menisectomies with joint debridement. Range of motion prior to surgery was as follows: maximum opening—43 mm; lateral excursion to right—5 mm; lateral excursion to left—7 mm. Rehabilitation utilizing the methodology and apparatus of the invention was provided for seven consecutive days and obtained the following range of motin: maximum opening—43 mm; right lateral excursion—9 mm; left lateral excursion—11 mm. Patient related an approximate 80% reduction of pain.

EXAMPLE II

A 27 year old female with a fifteen year history of left temporomandibular joint pain and limited motion. Previous patient treatment invovled a series; of intra oral devices, tooth equilibration restorative dentistry, medication and physical therapy. A diagnosis based on history, examination, corrected serial tomograms and arthrograms indicated a chronic closed lock with moderate degenerative joint disease, left temporomandibular joint. The arthrogram revealed a perforation of the articular brisc. A menisectomy was conducted. Prior to surgery, the patient exhibited the following range of motion: maximum opening—35 mm; right lateral excursion—7 Iron; left lateral excursion—6 Rehabilitation utilizing the methodology and apparatus of the invention was conducted for eight days of consecutive therapy and at the end of rehabilitation the range of motion was as follows: maximum opening—43 mm; right lateral excursion—9 mm; left lateral excursion—9 mm. The patient used the device intermittently over the following two months and at the end of two months the range of motion was as follows: maximum opening—43 mm; right lateral excursion—11 mm; left lateral excursion—11 mm. The patient related an approximate 90% reduction of pain.

EXAMPLE III

A 44 year old female with a long history of right sided temporomandibular joint pain. Prior to presentation, the patient had undergone two open joint surgeries on the right side, both being disc plications. The workup consisted of corrected serial tomograms, history and examination. A diagnosis of fibrous-bony ankylosis was indicated. Range of motion prior to surgery was as follows: maximum opening—11 mm; right lateral excursion—4 mm; left lateral excursion—0 mm. The patient had a marked deviation on opening to the left side. Patient underwent a menisectomy and debridement. Immediately after surgery, patient was started on rehabilitation using the methodology and apparatus of the invention. After two weeks, motion Was as follows: maximum opening—31 mm; right lateral excursion—9 mm; left lateral excursion—5 mm. Patient had less deviation to the left side. No attempt was made to force the patient's mouth open and only translatory motion was emphasized. Patient related a 50% to 60% reduction of pain.

EXAMPLE IV

A 23 year old male with a previous history of a fractured mandible. Approximately two years after sustaining trauma, patient incurred severe bilateral joint pain and limited motion. Patient was treated with a series of intra oral splints and physical therapy with no apparent improvement. Patient underwent surgery approximately one year prior to presentation. Both joints were subjected to surgery twice with the last surgery involving bilateral proplast implants. Diagnosis involved advanced degenerative joint disease and fibrous ankylosis, both left and right temporomandibular joints. Patient underwent bilateral joint surgery consisting of removal of proplast implants, joint debridement and arthroplasty. Prior to surgery, the range of motion was as follows: maximum opening—7 mm; left lateral excursion—2 mm; right lateral excursion—2 mm. Following surgery the patient was rehabilitated according to the invention for approximately seven weeks. At the end of that time period, range of motion was as follows: maximum opening—40 mm; left lateral excursion—6 mm; right lateral excursion—7 mm. Patient related an approximate 80% reduction of symptoms.

EXAMPLE V

A 45 year old male involved in a motor vehicle accident involving sustainment of multiple facial fractures including multiple fractures of mandible and maxilla with the right mandibular condyle being displaced into the cranial base. Four months after both open and closed reductions of facial fractures, patient developed a fibrous and bony ankylosis of time right mandibular condyle along with ankylosis of the right coronoid process and temporalis muscles with advanced adhesions around time right pterygoid plates and medial surface of the mandible. The patient shortly underwent a menisectomy and arthroplasty of the right temporomandibular joint, coronoidectomy of the right side with freeing of adhesions between the right pterygoid plate and ramus of the mandible. Prior to surgery, opening was as follows: maximum opening—4 mm; left lateral excursion—0 mm; right lateral excursion—4 mm. Immediately after surgery the patient was rehabilitated according to the invention for approximately five weeks. At the end of five weeks, range of motion was as follows: maximum opening 25 mm; left lateral excursion—6 mm; right lateral excursion—6 mm. Patient had only a slight reduction in pain as pain was never a problem, the problem being a matter of severe limited range of motion.

EXAMPLE VI

A 33 year old female with a six year history of bilateral temporomandibular joint pain and associated headaches. Treatment previously consisted of orthognathic surgery to correct a Class II malocclusion, arthroscopy being undertaken twice on the left side and once on the right side. Patient also had a series of intraoral devices and physical therapy. Patient's primary complaint was bilateral joint pain with associated headaches. Diagnosis based on serial tomograms and arthrograms revealed advanced degenerative joint disease with chronic closed lock and fibrous ankylosis of the left joint and moderate degenerative joint disease with displaced disc and moderate intracapsular adhesions of the right joint. Patient underwent bilateral menisectomies and an arthroplasty on the left side. Prior to surgery, range of motion was as follows: maximum opening—15 mm; right lateral excursion—1 to 2 mm; left lateral excursion—3 mm. Immediately after surgery the patient was rehabilitated according to the invention and the following range of motion was obtained: maximum opening—43 mm; right lateral excursion—8 mm; left lateral excursion—8 mm. The patient related a 75% reduction in symptomology.

EXAMPLE VII

A 39 year old male in an industrial accident sustained trauma to the left temporomandibular joint. Previous treatment consisted of multiple intra oral splints, medications, physical therapy and four surgeries conducted on the left joint consisting of reconstructive arthroplasty, arthroscopy, placement of sylastic implant and removal of sylastic implant. Diagnosis involved bony-fibrous ankylosis and advanced degenerative joint disease of the left temporomandibular joint. The patient underwent menisecotmy, debridement and arthroplasty. Prior to surgery range of motion was as follows: maximum opening—25 mm; right lateral excursion—3 mm; left lateral excursion—5 mm with marked deviation on opening to the left. immediately after surgery, rehabilitation was conducted according to the invention and after two weeks the following range of motion was obtained: maximum opening—35 mm; right lateral excursion—8 mm; left lateral excursion—11 mm with degree of deviation to the left side being markedly reduced. Patient related that his temporomandibular joint pain was 90% reduced but his primary complaint of headaches which began shortly after the accident remained essentially the same.

EXAMPLE VIII

A 33 year old female who was assaulted with resultant trauma to both left and right temporomandibular joints. Patient's primary complaint following the injury was bilateral joint pain and limited range of motion. Patient underwent therapy with intra oral devices and physical therapy without relief. Diagnosis based on history, examination, corrected tomograms and arthrograms showed early degenerative joint changes with moderate fibrous adhesions and interal derangement bilaterally. Approximately three years after the accident, the patient underwent bilateral menisectomies, joint debridement and arthroplasty. Range of motion following surgery was slightly decreased over normal. Three years after surgery, the patient returned complaining of right-sided joint pain and limited motion. Range of motion was measured as follows: maximum opening—31 mm; right lateral excursion—5 mm; left lateral excursion—2 mm. The patient tried for approximately four weeks using apparatus configured according to the invention but without surgery and the following range of motion was obtained: maximum opening—41 mm; right lateral excursion—8 mm; left lateral excursion—8 mm. Patient related an 80% to 90% reduction of symptomology.

EXAMPLE IX

A 39 year old female with primary complaint of pain in the left temporomandibular joint and limited motion. Patient had a previous diagnosis of closed lock, left temporomandibular joint. Patient also exhibited a facial asymmetry due to approximately 12 mm of condylar loss on the left side. Patient previously received a treatment plan consisting of condylatomy with intermaxillary fixation followed by orthodontic therapy and mandibular and maxillary osteotomies. Patient sought a second opinion for the treatment. Patient also had previously undergone recurrent bouts of acute synovitis in the left joint. At time of presentation, range of motion was as follows: maximum opening—24 mm; right lateral excursion—6 mm; left lateral excursion—8 mm. Patient underwent therapy only with use of the methodology and apparatus of the invention and used the apparatus of the invention for approximately one and a half weeks. Range of motion at the end of therapy being as follows: maximum opening—38 mm; right lateral excursion—10 mm; left lateral excursion—11 mm. Patient related approximately 50% reduction of symptomology.

EXAMPLE X

A 70 year old male related no temporomandibular joint dysfunction prior to tooth extraction. Shortly after tooth extraction patient noticed a decrease in range of motion. Pain was not a significant complaint. Diagnosis based on history, examination, corrected serial tomograms and arthrograms showed an acute closed lock. Range of motion was as follows: maximum opening—17 mm; right lateral excursion—5 mm; left lateral excursion—9 mm. Without other treatment, patient was treated according to the methodology of the invention and an apparatus configured according to the invention. After one month, the following range of motion was obtained: maximum opening—42 mm; right lateral excursion—9 mm; left lateral excursion—10 mm. Since pain was not a significant problem, no quantification of pain reduction was indicated.

Since continuous passive motion (also known widely as CPM) according to the invention involves translatory motion having components of motion in both side-to-side and front-to-back senses, it is to be understood that the invention encompasses such motions both with or without a component of motion in the other sense. The apparatus of the invention can be configured within the framework of structure herein presented to effect such motion. The methodology of the invention is further understood to encompass such motion.

While the methodology and apparatus of the invention have been described in relation to certain protocols and embodiments of an apparatus, it is to be understood that the invention can be practiced other than as explicitly described wtihout departing from the scope of the invention, the invention being defined according to the recitations of the appended claims.

What is claimed is:

1. An apparatus for rehabilitation of the temporomandibular joint comprising means for engaging the mandible of a user and effecting means connected to the mandible-engaging means for effecting only translatory motion of the joint, the translatory motion of the joint being effected through motion imparted to the mandible-engaging means by the effecting means.

2. The apparatus of claim 1 wherein the effecting means causes the motion to be effected forwardly of centric occlusion.

3. The apparatus of claim 1 wherein the effecting means causes the motion to be effected continuously and passively.

4. The apparatus of claim 1 wherein the effecting means comprise:

means connected to the effecting means for engaging the upper jaw of a user and for maintaining the upper jaw in a stationary position.

5. The apparatus of claim 4 wherein the effecting means further comprises body support means and wherein the upper jaw-engaging means comprise:

plate means connected to the body support means; and, a registration attached to the distal end of the plate means, the registration bearing an impression of the teeth or that structure extending into the mouth from the upper jaw, the registration receiving the teeth or said structure on insertion of the plate means into the mouth.

6. The apparatus of claim 5 wherein the plate means comprise:

a body portion having a cut-out portion;

track elements oppositely disposed within the cut-out portion; and, adjustment means movable along the track elements and longitudinally of the plate means for adjustment of the position of the upper jaw-engaging means relative to the mandible-engaging means; and, means for fixing the adjustment means at a desired location within the cut-out means.

7. The apparatus of claim 6 wherein the adjustment means comprise an adjustment plate having parallel U-shaped channels defined one each along opposite edges of said adjustment plate, the adjustment plate being movable along the track elements, and wherein the adjustment plate is provided with a hole disposed centrally therethrough for receiving at least a portion of the motion imparting means.

8. The apparatus of claim 7 wherein the plate means further comprise connecting means fixedly attached to the anterior end of the plate means and fixedly attached to the body support means for rendering the plate means fixed relative to the body support means.

9. The apparatus of claim 4 wherein the effecting means further comprise body support means and wherein the mandible-engaging means comprise:

plate means; and, a registration attached to the distal end of the plate means, the registration bearing an impression of the teeth or that structure extending into the mouth from the mandible, the registration receiving the teeth or said structure on insertion of the plate means into the mouth.

10. The apparatus of claim 7 wherein the plate means comprise a body portion having a centrally disposed circular cut-out portion and wherein the motion imparting means comprise a driven shaft and double eccentric means operable with the shaft and receivable within the cut-out portion and fixed to the body portion for imparting motion to the plate means and therefore to the registration attached to the plate means.

11. The apparatus of claim 10 wherein the double eccentric means comprise:

a major circular eccentric receivable within the circular cut-out portion of the body portion and adjustably fixed therein, the major eccentric having a circular cut-out portion formed therein which is off-center of the major eccentric; and, a minor circular eccentric receivable within the circular cut-out portion formed in the major eccentric and adjustably fixed therein, the minor eccentric having a circular cut-out portion formed therein which is off-center of the minor eccentric, the driven shaft being fixed within the circular cut-out portion, the major and minor eccentrics being rotatable relative to each other to positions causing the mandible engaging means to be capable of varying degrees of motion.

12. The apparatus of claim 11 wherein the motion imparting means further comprise:

a motor and a drive shaft driven by the motor;

gear reduction means disposed within the body support means and connected to the driven shaft for reducing the rotational speed of the driven shaft from the rotational speed of the drive shaft; and, universal joint means connecting the drive shaft to the driven shaft for providing a degree of angular flexibility between the drive shaft and the driven shaft.

13. The apparatus of claim 12 and further comprising a switch controlling the motor for actuating the drive shaft and for reversing the direction of rotation of the motor, the switch being actuable on holding of the switch and discontinuing operation of the apparatus on release of the switch.

14. The apparatus of claim 12 and further comprising a housing for the motor, the housing being shaped to be received within and graspable by the hand of a user.

15. The apparatus of claim 4 wherein the effecting means causes the motion to be effected continuously and passively.

16. The apparatus of claim 1 and further comprising means for varying the speed of the motion of the joint.

17. The apparatus of claim 1 and further comprising means for varying the degree of motion of the joint.

18. An apparatus for rehabilitation of the temporomandibular joint comprising means for effecting translatory motion of the joint, the effecting means comprising body support means, means for engaging the upper jaw of a user and for maintaining the upper jaw in a stationary position, the upper jaw-engaging means comprising plate means connected to the body support means and a registration attached to the distal end of the plate means, the registration bearing an impression of the teeth or that structure extending into the mouth from the upper jaw, the registration receiving the teeth or said structure on insertion of the plate means into the mouth, means connected to the body support means for engaging the mandible of a user, and, means connected to the mandible-engaging means for imparting motion to said mandible-engaging means and, through the mandible-engaging means, for imparting a translatory motion to the joint.

19. The apparatus of claim 18 wherein the effecting means causes the motion to be effected forwardly of centric occlusion.

20. The apparatus of claim 18 wherein the effecting means causes the motion to be effected continuously and passively.

21. The apparatus of claim 18 wherein the mandible-engaging means comprise second plate means and a second registration attached to the distal end of the second plate means, the second registration bearing an impression of the teeth or that structure extending into the mouth from the mandible, the second registration receiving the teeth or said structure on insertion of the second plate means into the mouth.

22. An apparatus for rehabilitation of the temporomandibular joint comprising means for effecting translatory motion of the joint, the effecting means comprising body support means, means for effectively engaging the mandible of the user, the mandible-engaging means comprising plate means connected to the body support means and a registration attached to the distal end of the plate means, the registration bearing an impression of the teeth or that structure extending into the mouth from the mandible, the registration receiving the teeth or said structure on insertion of the plate means into the mouth, and, means connected to the mandible-engaging means for imparting motion to said mandible-engaging means and, through the mandible-engaging means, for imparting a translatory motion to the joint.

23. The apparatus of claim 22 wherein the effecting means further comprise means for engaging the upper jaw of a user and for maintaining the upper jaw in a stationary position.

24. The apparatus of claim 22 wherein the effecting means causes the motion of the joint to be effected passively.

25. The apparatus of claim 22 wherein the effecting means causes the motion of the joint to be effected both continuously and passively.

26. The apparatus of claim 22 wherein the effecting means causes the motion to be effected continuously during a therapeutically useful period of time.

27. The apparatus of claim 25 wherein the effecting means causes the motion of the joint to be effected for a therapeutically useful period of time and degree of motion.

28. The apparatus of claim 25 wherein the effecting means causes the motion of the joint to be effected forwardly of centric occlusion.

29. The apparatus of claim 22 wherein the plate means comprise a body portion having a centrally disposed cut-out portion and wherein the motion-imparting means comprise a driven shaft and cam means operable with the shaft and receivable within the cut-out portion and fixed to the body portion for imparting motion to the plate means and therefore to the registration attached to the plate means.

30. The apparatus of claim 29 wherein the motion-imparting means comprises an additional driven shaft and gear means disposed within the body support means and connected to the driven shafts for selecting an operational speed of the effecting means depending upon selection of the driven shaft which is to be driven.

31. An apparatus for rehabilitation of the temporomandibular joint comprising means for effecting continuously and passively translatory motion of the joint, the effecting means comprising, means for effectively engaging the mandible of a user, the mandible-engaging means comprising a plate element having a distal end and a proximal end and a registration attached to the distal end of the plate element, the registration bearing an impression of the teeth or of that structure extending into the mouth from the mandible, the registration receiving the teeth or said structure on insertion of the distal end of the plate element into the mouth of a user, and, means connected to the mandible-engaging means for imparting motion to said mandible-engaging means and thus a translatory motion to the joint.

32. The apparatus of claim 31 wherein the motion-imparting means is connected to the plate element in proximity to the proximal end of the plate element, the motion-imparting means comprising an eccentric cam fixed to the plate element, a driven shaft connected to the eccentric cam and means for driving the shaft, rotation of the shaft imparting motion to the cam and thus to the plate element to move the registration in a translatory motion, thereby moving the mandible of the user in a translatory motion.

33. The apparatus of claim 32 wherein the plate element has an aperture formed in the proximal end thereof, the eccentric cam being fitted into the aperture formed in the plate element, the eccentric cam having an aperture formed therein for receiving a portion of the driven shaft.

34. The apparatus of claim 33 wherein the eccentric cam is substantially circular and a central portion of the aperture formed in the eccentric cam is located along a diameter of the cam and spaced from the center of the cam.

35. The apparatus of claim 34 and further comprising a plurality of eccentric cams each having the aperture formed in each said cam spaced from the center of the cam at differing distances, substitution of each cam into the aperture formed in the plate element causing the motion-imparting means to vary the degree of motion of the registration formed on the distal end of the plate element and thus the mandible of the user.

36. The apparatus of claim 31 wherein the motion-imparting means comprises means for varying the speed of the motion of the joint.

37. The apparatus of claim 32 wherein the motion-imparting means comprises means for varying the speed of the motion of the joint.

38. The apparatus of claim 34 wherein the motion-imparting means comprises means for varying the speed of the motion of the joint.

39. The apparatus of claim 31 wherein the motion-imparting means comprises means for varying the degree of motion of the joint.

40. The apparatus of claim 32 wherein the motion-imparting means comprises means for varying the degree of motion of the joint.

41. The apparatus of claim 41 and further comprising a second plate element engaging the upper jaw of a user and having a second registration attached to the distal end thereof, the registration bearing an impression of the teeth or that structure extending into the mouth from the upper jaw, the second registration receiving the teeth or said structure on insertion of the distal end of the second plate element into the mouth of the user, the second plate element being stationary relative to the first-mentioned plate element on motion of the first-mentioned plate element to maintain the upper jaw of the user in a stationary position relative to the mandible of the user.

42. The apparatus of claim 41 wherein the motion-imparting means comprises means for varying the degree of motion of the joint.

43. The apparatus of claim 41 wherein the motion-imparting means comprises means for varying the speed of the motion of the joint.

* * * * *